(12) United States Patent
Yazaki et al.

(10) Patent No.: US 7,776,330 B2
(45) Date of Patent: Aug. 17, 2010

(54) HUMANIZED ANTI-CEA T84.66 ANTIBODY AND USES THEREOF

(75) Inventors: Paul J. Yazaki, Glendale, CA (US);
Mark A. Sherman, Pasadena, CA (US);
John E. Shively, Arcadia, CA (US);
Andrew A. Raubitschek, San Marino, CA (US); Anna M. Wu, Sherman Oaks, CA (US)

(73) Assignee: City of Hope, Duarte, CA (US)

( * ) Notice: Subject to any disclaimer, the term of this patent is extended or adjusted under 35 U.S.C. 154(b) by 287 days.

(21) Appl. No.: 11/861,093

(22) Filed: Sep. 25, 2007

(65) Prior Publication Data

US 2008/0069816 A1 Mar. 20, 2008

Related U.S. Application Data

(62) Division of application No. 11/077,978, filed on Mar. 11, 2005, now Pat. No. 7,273,608.

(60) Provisional application No. 60/552,538, filed on Mar. 11, 2004.

(51) Int. Cl.
*A61K 39/395* (2006.01)
*C12P 21/04* (2006.01)
*C12P 21/08* (2006.01)
*C07K 16/00* (2006.01)

(52) U.S. Cl. .............. 424/133.1; 424/141.1; 424/156.1; 424/181.1; 424/183.1; 435/69.6; 435/70.21; 530/387.3; 530/388.1; 530/388.85; 530/391.7

(58) Field of Classification Search ........................ None
See application file for complete search history.

(56) References Cited

U.S. PATENT DOCUMENTS 5,639,641 A 6/1997 Pedersen et al.
6,639,055 B1 10/2003 Carter et al.

OTHER PUBLICATIONS

Wong et al. The Journal of Nuclear Medicine, 39(12):2097-2104. Dec. 1998.*
Beatty, J.D., et al. "Preoperative imaging of colorectal carcinomas with $^{111}$In-labeled anti-carcinoma antigen monoclonal antibody." *Cancer Res.* 46:6494-6502 (1986).
Bebbington, C., et al. "High-level expression of a recombinant antibody from myeloma cells using a glutamine synthetase gene as an amplifiable selection marker." *Biotechnology* 10:169-175 (1992).
Berman, H.M., et al. "The Protein Data Bank." *Nucleic Acids Res.* 28:235-242 (2000).
Bernstein, F., et al. "The Protein Data Bank: A computer-based archival file for macromolecular structures." *J. Mol. Biol.* 112:535-542 (1977).
Blumenthal, R.D., et al. "Carcinoembryonic antigen antibody inhibits lung metastasis and augments chemotherapy in a human colonic carcinoma xenograft." *Cancer Immunol. Immunother.* 54:315-327 (2005).
Bruggemann, M., et al. "Human antibody production in transgenic mice: expression from 100 kb of the human IgH locus." *Eur. J. Immunol.* 21:1323-1326 (1991).
Carmichael, J.A., et al. "The crystal structure of an anti-CEA scFv diabody assembled from T84.66 scFvs in V(L)-to-V(H) orientation: implications for diabody flexibility." *J. Mol. Biol.* 326:341-351 (2003).
Chothia, C., et al. "Canonical structures for the hypervariable regions of immunoglobulins." *J. Mol. Biol.* 196:901-917 (1987).
D'Argenio, D.Z., et al. "A program package for simulation and parameter estimation in pharmacokinetic systems." *Comput. Programs Biomed.* 9:115-134 (1979).
Eigenbrot, C., et al. "X-ray structures of the antigen-binding domains from three variants of humanized anti-p185$^{HER2}$ antibody 4D5 and comparison with molecular modeling." *J. Mol. Biol.* 229:969-995 (1993).
Eigenbrot, C., et al. "X-Ray structures of fragments from binding and nonbinding versions of a humanized anti-CD18 antibody: structural indications of the key role of VH residues 59 to 65." *Proteins* 18:49-62 (1994).
Foote, J., et al. "Antibody framework residues affecting the conformation of the hypervariable loops." *J. Mol. Biol.* 224:487-499 (1992).
Gibrat, J.F., et al. "Surprising similarities in structure comparison." *Curr. Opin. Struct. Biol.* 6:377-385 (1996).
Horton, R.M., et al. "Engineering hybrid genes without the use of restriction enzymes: gene splicing by overlap extension." *Gene* 77:61-68 (1989).
Huang, E.H., et al. "CEA-based vaccines." *Expert Rev. Vaccines* 1:49-63 (2002).
Imikare, T., et al. "Generation, immunologic characterization and antitumor effects of human monoclonal antibodies for carcinoembryonic antigen." *Int. J. Cancer* 108:564-570 (2004).
Johnson, G., et al. "Kabat database and its applications: future directions." *Nucleic Acid Res.* 29:205-206 (2001).
Jones, P.T., et al. "Replacing complementarity-determining regions in a human antibody with those from a mouse." *Nature* 321:522-525 (1986).
Laemmli, U. "Cleavage of structural protein during the assembly of the head of bacteriophage T4." *Nature* 227:680-685 (1970).
Low, N.M., et al. "Mimicking somatic hypermutation: affinity maturation of Antibodies Displayed on Bacteriophage Using a Bacterial Mutator Strain." *J. Mol. Biol.* 260:359-368 (1986).
MacCallum, R.M., et al. "Antibody-antigen interactions: contact analysis and binding site topography." *J. Mol. Biol.* 262:732-745 (1996).

(Continued)

*Primary Examiner*—David J. Blanchard
(74) *Attorney, Agent, or Firm*—Perkins Coie LLP; Patrick D. Morris

(57) ABSTRACT

Embodiments of the present invention utilize a more efficient CDR grafting technique to generate humanized versions of the T84.66 antibody. The technique used to generate these antibodies utilizes crystallographic structural data to select an immunoglobulin framework having maximum structural overlap with a non-human donor molecule. This technique was used to develop humanized T84.66 antibodies exhibiting in vitro binding affinity and specificity for carcinoembryonic antigen (CEA) nearly identical to that of T84.66 and the ability to specifically target tumors expressing CEA in vivo.

9 Claims, 8 Drawing Sheets

OTHER PUBLICATIONS

Marshall, J. "Carcinoembryonic antigen-based vaccines." *Semin. Oncol.* 30(3 Suppl 8):30-36 (2003).

Maynard J., et al. "Antibody Engineering." *Annu. Rev. Biomed. Eng.* 2:339-376 (2000).

Mendez, M.J., et al. "Functional transplant of megabase human immunoglobulin loci recapitulates human antibody response in mice." *Nat. Genet.* 2:146-156 (1997).

Morea, V.T.A., et al. "Conformations of the third hypervariable region in the VH domain of immunoglobulins." *J. Mol. Biol.* 275:269-294 (1998).

Morton, B.A., et al. "Artifactual CEA elevation due to human anti-mouse antibodies." *Arch. Surg.* 123:1242-1246 (1988).

Neumaier, M., et al. "Cloning of the genes for T84.66, an antibody that has a high specificity and affinity for carcinoembryonic antigen, and expression of chimeric human/mouse T84.66 genes in myeloma and Chinese hamster ovary cells." *Cancer Res.* 50:2128-2134 (1990).

O'Brien, S., et al. "Humanization of monoclonal antibodies by CDR grafting." *Methods Mol .Biol.* 207:81-100 (2003).

O'Connor, et al. "Humanization of an antibody against human protein C and calcium- dependence involving framework residues." *Protein Eng.* 11:321-328 (1998).

Padlan, E.A., et al. "Identification of specificity-determining residues in antibodies." *FASEB J.* 9:133-139 (1995).

Schroff, R.W., et al. "Human anti-murine responses in patients receiving monoclonal antibody therapy." *Cancer Res.* 45:879-885 (1985).

Shawler, D.L., et al. "Human immune response to multiple injections of murine monoclonal immunoglobulins." *J. Immunol.* 135:1530-1535 (1985).

Wagener, C., et al. "Monoclonal antibodies for carcinoembryonic antigen and related antigens as a model system: determination of affinities and specificities of monoclonal antibodies by using biotin-labeled antibodies and avidin as precipitating agent in a solution phase immunoassay." *J. Immunol.* 130:2302-2307 (1983).

Winter, G., et al. "Making antibodies by phage display technology." *Annu. Rev. Immunol.* 12:433-455 (1994).

Wong, J.Y.C., et al. "Initial experience evaluating $^{90}$yttrium-radiolabeled anti-carcinoembryonic antigen chimeric T84.66 in a phase I radioimmunotherapy trial." *Cancer Res.* 55(23 Suppl):5929s-5934s (1995).

Wong, J.Y.C., et al. "Clinical evaluation of indium-111-labeled chimeric anti-CEA monoclonal antibody." *J. Nucl. Med.* 38:1951-1959 (1997).

Wong, J.Y.C., et al. "Initial clinical experience evaluating yttrium-90-chimeric T84.66 anticarcinoembryonic antigen antibody and autologous hematopoietic stem cell in patients with carcinoembryonic antigen-producing metastatic breast cancer." *Clin. Cancer Res.* 5(10 Suppl):3224s-3231s (1999).

Wu, T.T., et al. "An analysis of the sequences of the variable regions of Bence Jones proteins and myeloma light chains and their implications for antibody complementarity." *J. Exp. Med.* 132:211-250 (1970).

Wu, A.M., et al. "Tumor localization of anti-CEA single-chain Fvs: improved targeting by noncovalent dimers." *Immunotechnology* 2:221-236 (1996).

Xiang, J., et al. "Framework residues 71 and 93 of the chimeric B72.3 antibody are major determinants of the conformation of heavy-chain hypervariable loops." *J. Mol. Biol.* 253:385-390 (1995).

Yazaki, P.J., et al. "Mammalian expression and hollow fiber bioreactor production of recombinant anti-CEA diabody and minibody for clinical applications." *J. Immunol. Methods* 253:195-208 (2001).

You, Y.H., et al. "Expression, purification, and characterization of a two domain carcinoembryonic antigen minigene (N-A3) in *Pichia pastoris*. The essential role of the N-domain." *Anticancer Res.* 18:3192-3202 (1998).

Hu et al. Minibody: A Novel Engineered Anti-Carcinoembryonic Antigen Antibody Fragment (Single-Chain Fv-$C_H3$) Which Exhibits Rapid, High-Level Targeting of Xenografts, Cancer Research 1996, vol. 56:3055-3061.

Wong et al. A phase I trial of $^{90}$Y-Anti-Carcinoembryonic Antigen Chimeric T84.66 Radioimmunotherapy with 5-Fluorouracil in Patients with Metastatic Colorectal Cancer, Clinical Cancer Research, Dec. 2003, vol. 9, 5842-5852.

Bowie et al., Science, 247:1306-1310, 1990, p. 1306, col. 2.

Gussow et al., 1991, Methods in Enzymotology 203:99-121.

Rudikoff et al., PNAS, USA, 1982, 79: 1979.

Neumaier et al., 1990 Cancer Research 50:2128-2134.

Willuda et al., 1999, Cancer Research 59:5758-5767.

* cited by examiner

VL

```
                                                       CDR-L1
               1         10        20         27 a b c d  30
T84.66:     DIVLTQSPASLAVSLGQRATMSC<RAGESVDIFGVGFLH>
Herceptin:  DIQMTQSPSSLSASVGDRVTITC<RASQDVN----TAVA>
M5A/M5B:    DIQLTQSPSSLSASVGDRVTITC<RAGESVDIFGVGFLH>

CDR-L2
                     40        50        60        70
T84.66:     WYQQKPGQPPKLLIY<RASNLES>GIPVRFSGTGSRTDF
Herceptin:  WYQQKPGKAPKLLIY<SASFLYS>GVPSRFSGSRSGTDF
M5A/M5B:    WYQQKPGKAPKLLIY<RASNLES>GVPSRFSGSGSRTDF CDR-L3
                    80        90        100
T84.66:     TLIIDPVEADDVATYYC<QQTNEDPYT>FGGGTKLEIK
Herceptin:  TLTISSLQPEDFATYYC<QQHYTTPPT>FGQGTKVEIK
M5A/M5B:    TLTISSLQPEDFATYYC<QQTNEDPYT>FGQGTKVEIK
```

VH

```
                                                    CDR-H1
               1         10        20        30          40
T84.66:     EVQLQQSGAELVEPGASVKLSCTASGFNIK<DTYMH>WVKQR
Herceptin:  EVQLVESGGGLVQPGGSLRLSCAASGFNIK<DTYIH>WVRQA
M5A/M5B:    EVQLVESGGGLVQPGGSLRLSCAASGFNIK<DTYMH>WVRQA CDR-H2
                     50  52 a      60        70
T84.66:     PEQGLEWIG<RIDPANGNSKYVPKFQG>KATITADTSSNTAY
Herceptin:  PGKGLEWVA<RIYPTNGYTRYADSVKG>RFTISADTSKNTAY
M5A:        PGKGLEWVA<RIDPANGNSKYADSVKG>RFTISADTSKNTAY
M5B:        PGKGLEWVA<RIDPANGNSKYVPKFQG>RATISADTSKNTAY CDR-H3
              80 82 a b c      90          100a b c d         110
T84.66:     LQLTSLTSEDTAVYYCAP<FGYYVSDYAMAY>WGQGTSVTVSS
Herceptin:  LQMNSLRAEDTAVYYCSR<WGGDGFYAM-DY>WGQGTLVTVSS
M5A/M5B:    LQMNSLRAEDTAVYYCAP<FGYYVSDYAMAY>WGQGTLVTVSS
```

FIG 3

SEQUENCE LISTING

<160> NUMBER OF SEQ ID NOS: 31

<210> SEQ ID NO 1
<211> LENGTH: 111
<212> TYPE: PRT
<213> ORGANISM: Artificial
<220> FEATURE:
<223> OTHER INFORMATION: Artificially constructed variable light chain
      of M5A and M5B humanized antibodies

<400> SEQUENCE: 1

Asp Ile Gln Leu Thr Gln Ser Pro Ser Ser Leu Ser Ala Ser Val Gly
1               5                   10                  15

Asp Arg Val Thr Ile Thr Cys Arg Ala Gly Glu Ser Val Asp Ile Phe
                20                  25                  30

Gly Val Gly Phe Leu His Trp Tyr Gln Gln Lys Pro Gly Lys Ala Pro
            35                  40                  45

Lys Leu Leu Ile Tyr Arg Ala Ser Asn Leu Glu Ser Gly Val Pro Ser
    50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Thr Asn
                85                  90                  95

Glu Asp Pro Tyr Thr Phe Gly Gln Gly Thr Lys Val Glu Ile Lys
                100                 105                 110

<210> SEQ ID NO 2
<211> LENGTH: 121
<212> TYPE: PRT
<213> ORGANISM: Artificial
<220> FEATURE:
<223> OTHER INFORMATION: Artificially constructed variable heavy chain
      of M5A humanized antibody

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Met His Trp Val Arg Gln Ala Pro Gly Lys Gly Leu Glu Trp Val
        35                  40                  45

Ala Arg Ile Asp Pro Ala Asn Gly Asn Ser Lys Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser
            115                 120

<210> SEQ ID NO 3
<211> LENGTH: 121
<212> TYPE: PRT
<213> ORGANISM: Artificial
<220> FEATURE:
<223> OTHER INFORMATION: Artificially constructed variable heavy chain
      of M5B humanized antibody

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Met His Trp Val Arg Gln Ala Pro Gly Lys Gly Leu Glu Trp Val
        35                  40                  45

Ala Arg Ile Asp Pro Ala Asn Gly Asn Ser Lys Tyr Val Pro Lys Phe
    50                  55                  60

Gln Gly Arg Ala Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser
            115                 120

<210> SEQ ID NO 4
<211> LENGTH: 111
<212> TYPE: PRT
<213> ORGANISM: Mus musculus
<300> PUBLICATION INFORMATION:
<308> DATABASE ACCESSION NUMBER: 1MOEA
<309> DATABASE ENTRY DATE: 2002-09-09
<313> RELEVANT RESIDUES IN SEQ ID NO: (1)..(111)

<400> SEQUENCE: 4

Asp Ile Val Leu Thr Gln Ser Pro Ala Ser Leu Ala Val Ser Leu Gly
1               5                   10                  15

Gln Arg Ala Thr Met Ser Cys Arg Ala Gly Glu Ser Val Asp Ile Phe
            20                  25                  30

Gly Val Gly Phe Leu His Trp Tyr Gln Gln Lys Pro Gly Gln Pro Pro
        35                  40                  45
```

```
Lys Leu Leu Ile Tyr Arg Ala Ser Asn Leu Glu Ser Gly Ile Pro Val
    50                  55                  60

Arg Phe Ser Gly Thr Gly Ser Arg Thr Asp Phe Thr Leu Ile Ile Asp
65                  70                  75                  80

Pro Val Glu Ala Asp Asp Val Ala Thr Tyr Tyr Cys Gln Gln Thr Asn
                85                  90                  95

Glu Asp Pro Tyr Thr Phe Gly Gly Gly Thr Lys Leu Glu Ile Lys
            100                 105                 110

<210> SEQ ID NO 5
<211> LENGTH: 121
<212> TYPE: PRT
<213> ORGANISM: Mus musculus
<300> PUBLICATION INFORMATION:
<308> DATABASE ACCESSION NUMBER: 1MOEA
<309> DATABASE ENTRY DATE: 2002-09-09
<313> RELEVANT RESIDUES IN SEQ ID NO: (120)..(240)

<400> SEQUENCE: 5

Glu Val Gln Leu Gln Gln Ser Gly Ala Glu Leu Val Glu Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Ser Lys Tyr Val Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Thr Ser Leu Thr Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Ser Val Thr Val Ser Ser
        115                 120

<210> SEQ ID NO 6
<211> LENGTH: 107
<212> TYPE: PRT
<213> ORGANISM: Artificial
<220> FEATURE:
<223> OTHER INFORMATION: Variable light chain of humanized
      anti-p185HER2 antibody 4D5,version 8

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
```

<210> SEQ ID NO 7
<211> LENGTH: 120
<212> TYPE: PRT
<213> ORGANISM: Artificial
<220> FEATURE:
<223> OTHER INFORMATION: Variable heavy chain of humanized
      anti-p185HER2 antibody 4D5, version 8

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 8
<211> LENGTH: 78
<212> TYPE: DNA
<213> ORGANISM: Artificial
<220> FEATURE:
<223> OTHER INFORMATION: Synthetic oligonucleotide

<400> SEQUENCE: 8
tcgatcgact ctagagccgc caccatggag acagacacac tcctgctatg ggtgctgctg    60
ctctgggttc caggttcc                                                  78

<210> SEQ ID NO 9
<211> LENGTH: 79
<212> TYPE: DNA
<213> ORGANISM: Artificial
<220> FEATURE:
<223> OTHER INFORMATION: Synthetic oligonucleotide

<400> SEQUENCE: 9
tgggtgctgc tgctctgggt tccaggttcc acaggtgaca ttcagctgac ccaatctcca    60
agctctttgt ccgcctctg                                                 79

<210> SEQ ID NO 10
<211> LENGTH: 79
<212> TYPE: DNA
<213> ORGANISM: Artificial
<220> FEATURE:
<223> OTHER INFORMATION: Synthetic oligonucleotide

<400> SEQUENCE: 10
cccaatctcc aagctctttg tccgcctctg tggggatagg gtcaccatc acctgcagag     60 ccggtgaaag tgttgatat                                                 79

```
<210> SEQ ID NO 11
<211> LENGTH: 79
<212> TYPE: DNA
<213> ORGANISM: Artificial
<220> FEATURE:
<223> OTHER INFORMATION: Synthetic oligonucleotide

<400> SEQUENCE: 11
cacctgcaga gccggtgaaa gtgttgatat ttttggcgtt gggttttttgc actggtacca      60 gcagaaacca ggaaaagct                                                    79

<210> SEQ ID NO 12
<211> LENGTH: 79
<212> TYPE: DNA
<213> ORGANISM: Artificial
<220> FEATURE:
<223> OTHER INFORMATION: Synthetic oligonucleotide

<400> SEQUENCE: 12
aagggacgcc agattctagg ttggatgcac gatagatgag gagtttggga gcttttcctg      60
gtttctgctg gtaccagtg                                                    79

<210> SEQ ID NO 13
<211> LENGTH: 79
<212> TYPE: DNA
<213> ORGANISM: Artificial
<220> FEATURE:
<223> OTHER INFORMATION: Synthetic oligonucleotide

<400> SEQUENCE: 13
ctaatggtga gggtgaagtc tgtcctagac ccggagccac tgaacctaga agggacgcca      60
gattctaggt tggatgcac                                                    79

<210> SEQ ID NO 14
<211> LENGTH: 79
<212> TYPE: DNA
<213> ORGANISM: Artificial
<220> FEATURE:
<223> OTHER INFORMATION: Synthetic oligonucleotide

<400> SEQUENCE: 14
attagtttgc tgacagtaat aggtggcgaa atcttccggc tgcagactgc taatggtgag      60
ggtgaagtct gtcctagac                                                    79

<210> SEQ ID NO 15
<211> LENGTH: 78
<212> TYPE: DNA
<213> ORGANISM: Artificial
<220> FEATURE:
<223> OTHER INFORMATION: Synthetic oligonucleotide

<400> SEQUENCE: 15
acgttttatc tcgagcttgg tcccctgtcc gaacgtgtac gggtcttcat tagtttgctg      60
acagtaatag gtggcgaa                                                     78

<210> SEQ ID NO 16
<211> LENGTH: 88
<212> TYPE: DNA
<213> ORGANISM: Artificial
<220> FEATURE:
<223> OTHER INFORMATION: Synthetic oligonucleotide

<400> SEQUENCE: 16
```

-continued tcgatcgact ctagagccgc caccatgaaa tgcagctggg ttatcttctt cctgatggca      60
gtggttacag gggtcaattc agaggttc                                         88

<210> SEQ ID NO 17
<211> LENGTH: 89
<212> TYPE: DNA
<213> ORGANISM: Artificial
<220> FEATURE:
<223> OTHER INFORMATION: Synthetic oligonucleotide

<400> SEQUENCE: 17
cagtggttac aggggtcaat tcagaggttc agctggtgga gtctgggggt ggccttgtgc      60
agccaggggg ctcactccgt ttgtcctgc                                        89

<210> SEQ ID NO 18
<211> LENGTH: 88
<212> TYPE: DNA
<213> ORGANISM: Artificial
<220> FEATURE:
<223> OTHER INFORMATION: Synthetic oligonucleotide

<400> SEQUENCE: 18
cagccagggg gctcactccg tttgtcctgc gcagcttctg gcttcaacat taaagacacc      60
tatatgcact gggtgcgtca ggcccctg                                         88

<210> SEQ ID NO 19
<211> LENGTH: 87
<212> TYPE: DNA
<213> ORGANISM: Artificial
<220> FEATURE:
<223> OTHER INFORMATION: Synthetic oligonucleotide

<400> SEQUENCE: 19
cctatatgca ctgggtgcgt caggcccctg gtaagggcct ggaatgggtt gcaaggattg      60
atcctgcgaa tggtaatagt aaatatg                                          87

<210> SEQ ID NO 20
<211> LENGTH: 89
<212> TYPE: DNA
<213> ORGANISM: Artificial
<220> FEATURE:
<223> OTHER INFORMATION: Synthetic oligonucleotide

<400> SEQUENCE: 20
aggtaggctg tgtttttgga tgtgtctgcg cttatagtga acggcccctt gacgctatcg      60
gcatatttac tattaccatt cgcaggatc                                        89

<210> SEQ ID NO 21
<211> LENGTH: 89
<212> TYPE: DNA
<213> ORGANISM: Artificial
<220> FEATURE:
<223> OTHER INFORMATION: Synthetic oligonucleotide

<400> SEQUENCE: 21
aggtaggctg tgtttttgga tgtgtctgcg cttatagtgg cacggccctg gaacttcggg      60
acatatttac tattaccatt cgcaggatc                                        89

<210> SEQ ID NO 22
<211> LENGTH: 88
<212> TYPE: DNA

```
<213> ORGANISM: Artificial
<220> FEATURE:
<223> OTHER INFORMATION: Synthetic oligonucleotide

<400> SEQUENCE: 22
accaaacgga gcacaataat agacggcagt gtcctcagca cgcaggctgt tcatctgcag      60
gtaggctgtg ttttggatg tgtctgcg                                         88

<210> SEQ ID NO 23
<211> LENGTH: 89
<212> TYPE: DNA
<213> ORGANISM: Artificial
<220> FEATURE:
<223> OTHER INFORMATION: Synthetic oligonucleotide

<400> SEQUENCE: 23
gagacggtga ccagggttcc ttgaccccag taggccatag catagtcaga cacgtagtaa      60
ccaaacggag cacaataata gacggcagt                                       89

<210> SEQ ID NO 24
<211> LENGTH: 88
<212> TYPE: DNA
<213> ORGANISM: Artificial
<220> FEATURE:
<223> OTHER INFORMATION: Synthetic oligonucleotide

<400> SEQUENCE: 24
ggtgctcttg ctcgaggggtg ccagggggaa gaccgatggg cccttagtgg aggctgagga     60
gacggtgacc agggttcctt gaccccag                                        88

<210> SEQ ID NO 25
<211> LENGTH: 333
<212> TYPE: DNA
<213> ORGANISM: Artificial
<220> FEATURE:
<223> OTHER INFORMATION: Artificially constructed coding sequence for
      variable light chain of M5A and M5B humanized antibodies

<400> SEQUENCE: 25
gacattcagc tgacccaatc tccaagctct ttgtccgcct ctgtggggga tagggtcacc      60
atcacctgca gagccggtga aagtgttgat atttttggcg ttgggttttt gcactggtac     120
cagcagaaac caggaaaagc tcccaaactc ctcatctatc gtgcatccaa cctagaatct     180
ggcgtccctt ctaggttcag tggctccggg tctaggacag acttcaccct caccattagc     240
agtctgcagc cggaagattt cgccacctat tactgtcagc aaactaatga agacccgtac     300
acgttcggac aggggaccaa ggtggagata aaa                                  333

<210> SEQ ID NO 26
<211> LENGTH: 363
<212> TYPE: DNA
<213> ORGANISM: Artificial
<220> FEATURE:
<223> OTHER INFORMATION: Artificially constructed coding sequence for
      variable heavy chain of M5A humanized antibodies

<400> SEQUENCE: 26
gaggttcagc tggtggagtc tgggggtggc cttgtgcagc caggggggctc actccgtttg     60 tcctgcgcag cttctggctt caacattaaa gacacctata tgcactgggt gcgtcaggcc    120
cctggtaagg gcctggaatg ggttgcaagg attgatcctg cgaatggtaa tagtaaatat    180
gccgatagcg tcaagggccg tttcactata agcgcagaca catccaaaaa cacagcctac    240
```

-continued

```
ctgcagatga acagcctgcg tgctgaggac actgccgtct attattgtgc tccgtttggt    300
tactacgtgt ctgactatgc tatggcctac tggggtcaag aaccctggt caccgtctcc     360 tca                                                                   363

<210> SEQ ID NO 27
<211> LENGTH: 363
<212> TYPE: DNA
<213> ORGANISM: Artificial
<220> FEATURE:
<223> OTHER INFORMATION: Artificially constructed coding region of
      variable heavy chain M5B humanized antibodies

<400> SEQUENCE: 27
gaggttcagc tggtggagtc tgggggtggc cttgtgcagc caggggggctc actccgtttg     60 tcctgcgcag cttctggctt caacattaaa gacacctata tgcactgggt gcgtcaggcc    120
cctggtaagg gcctggaatg ggttgcaagg attgatcctg cgaatggtaa tagtaaatat    180
gtcccgaagt tccagggccg tgccactata agcgcagaca catccaaaaa cacagcctac    240
ctgcagatga acagcctgcg tgctgaggac actgccgtct attattgtgc tccgtttggt    300
tactacgtgt ctgactatgc tatggcctac tggggtcaag aaccctggt caccgtctcc     360 tca                                                                   363

<210> SEQ ID NO 28
<211> LENGTH: 111
<212> TYPE: PRT
<213> ORGANISM: Mus musculus

<400> SEQUENCE: 28

Asp Ile Val Leu Thr Gln Ser Pro Ala Ser Leu Ala Val Ser Leu Gly
1               5                   10                  15

Gln Arg Ala Thr Met Ser Cys Arg Ala Gly Glu Ser Val Asp Ile Phe
            20                  25                  30

Gly Val Gly Phe Leu His Trp Tyr Gln Gln Lys Pro Gly Gln Phe Phe
        35                  40                  45

Lys Leu Leu Ile Tyr Arg Ala Ser Asn Leu Glu Ser Gly Ile Pro Val
    50                  55                  60

Arg Phe Ser Gly Thr Gly Ser Arg Thr Asp Phe Thr Leu Ile Ile Asp
65                  70                  75                  80

Pro Val Glu Ala Asp Asp Val Ala Thr Tyr Tyr Cys Gln Gln Thr Asn
                85                  90                  95

Glu Asp Pro Tyr Thr Phe Gly Gly Gly Thr Lys Leu Glu Ile Lys
            100                 105                 110

<210> SEQ ID NO 29
<211> LENGTH: 120
<212> TYPE: PRT
<213> ORGANISM: Mus musculus

<400> SEQUENCE: 29

Glu Val Gln Leu Gln Gln Ser Gly Ala Glu Leu Val Glu Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Phe Ala Asn Gly Trp Ser Lys Tyr Val Pro Lys Phe
```

```
                50                  55                  60
Gln Gly Met Ala Thr Ile Thr Ala Asp Thr Ser Ser Asn Thr Ala Tyr
 65                  70                  75                  80

Leu Gly Leu Thr Ser Leu Thr Ser Glu Asp Thr Ala Val Tyr Tyr Cys
                 85                  90                  95

Ala Pro Pro Gly Tyr Tyr Val Ser Asp Tyr Ala Met Thr Trp Gly Gln
                100                 105                 110

Gly Thr Ser Val Thr Val Ser Ser
            115                 120

<210> SEQ ID NO 30
<211> LENGTH: 107
<212> TYPE: PRT
<213> ORGANISM: Artificial
<220> FEATURE:
<223> OTHER INFORMATION: Artificially constructed variable light chain
      of Herceptin (Trastuzumab) humanized monoclonal antibody

<400> SEQUENCE: 30

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
                 20                  25                  30

Val Ala Trp Tyr Gln Gln Lys Pro Gly Lys Ala Pro Lys Leu Leu Leu
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
            100                 105

<210> SEQ ID NO 31
<211> LENGTH: 120
<212> TYPE: PRT
<213> ORGANISM: Artificial
<220> FEATURE:
<223> OTHER INFORMATION: Artificially constructed variable heavy chain
      of Herceptin (Trastuzumab) humanized monoclonal antibody

<400> SEQUENCE: 31

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
                 20                  25                  30

Tyr Ile His Trp Val Arg Gln Ala Pro Gly Lys Gly Leu Glu Trp Val
             35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Phe Ala Glu Asp Thr Ala Val Tyr Tyr Cys
                 85                  90                  95

Ser Arg Trp Gly Gly Asp Gly Phe Tyr Ala Met Asp Tyr Trp Gly Gln
                100                 105                 110
```

```
Gly Thr Leu Val Thr Val Ser Ser
        115                 120
```

HUMANIZED ANTI-CEA T84.66 ANTIBODY AND USES THEREOF

RELATED APPLICATIONS

The present application is a divisional of U.S. patent application Ser. No. 11/077,978, filed on Mar. 11, 2005 and issued as U.S. Pat. No. 7,273,608, which claims priority to U.S. Provisional Patent Application No. 60/552,538 (Yazaki et al.), filed on Mar. 11, 2004, the disclosures of both of which are incorporated by reference herein in their entirety, including drawings.

GOVERNMENT INTEREST

This invention was made with government support from the National Cancer Institute, program project grant CA 43904 and cancer core grant CA 33572.

FIELD OF THE INVENTION

The present invention relates to the fields of immunology, variant antibodies, molecular biology, recombinant DNA, cancer diagnosis, and cancer therapy. In particular, this invention provides a humanized antibody that recognizes the same antigen as the murine monoclonal antibody T84.66.

BACKGROUND

Antibodies are made up of two classes of polypeptide chains, light chains and heavy chains. A single naturally occurring antibody comprises two identical copies of a light chain and two identical copies of a heavy chain. The heavy chains, which each contain one variable domain and multiple constant domains, bind to one another via disulfide bonding within their constant domains to form the "stem" of the antibody. The light chains, which contain one variable domain and one constant domain, each bind to one heavy chain via disulfide binding. The variable domain of each light chain is aligned with the variable domain of the heavy chain to which it is bound. The variable regions of both the light chains and heavy chains contain three hypervariable regions sandwiched between four more conserved framework regions. These hypervariable regions, known as the complementary determining regions (CDRs), form loops that comprise the principle antigen binding surface of the antibody.

Monoclonal antibodies are antibodies that are derived from a single source or clone of cells that recognize only one antigen epitope. Generally, they are made by fusing an immortalized tumor cell with a mammalian immune cell to form a hybridoma cell that produces an antibody. This hybridoma cell is capable of producing a large quantity of a single antibody. The production of monoclonal antibodies is generally done using rat or mouse cells, but other species such as hamsters, sheep, and humans have been used. Monoclonal antibodies possess a variety of potential in vivo uses. For instance, labeled monoclonal antibodies that specifically recognize a particular tumor-associated antigen can be an extremely powerful diagnostic tool. One key issue for the in vivo therapeutic use of monoclonal antibodies has been the response of the human immune system to xenogeneic antibodies. Clinical studies with murine monoclonal antibodies have shown effective tumor targeting, but have also resulted in rapid clearance of the murine antibody due to the generation of a human anti-murine antibody (HAMA) immune response (Schroff 1985; Shawler 1985).

One solution to HAMA response problem is to generate human antibodies from human immunoglobulin phage display libraries (Winter 1994) or transgenic animals (Bruggemann 1991, Mendez 1997). These techniques have produced a small yet growing number of antibodies with high specificity and affinity. However, antibodies produced by these methods have either exhibited specificity only for immobilized antigen or have exhibited poor expression as intact antibodies in mammalian cell culture. The question remains to be answered in the clinic whether this new generation of engineered antibodies will be immunogenic, if not through a response to the foreign framework residues then as an anti-idiotypic response. Another solution to the HAMA response problem has been the use of recombinant methodologies to generate chimeric monoclonal antibodies, which generally consist of a murine antigen-binding variable domain coupled to a human constant domain. These chimeras have a lower frequency of immune response, but they are not effective for all antibodies and may still generate an immune response against the murine variable region. A third solution to the HAMA response problem is the utilization of humanized or reshaped monoclonal antibodies. These consist of human antibodies in which only the complementary determining region (CDR) has been substituted with an animal CDR region.

The current generation of humanized monoclonal antibodies approved for therapy are the result of grafting murine-derived CDR's onto a human antibody framework (Jones 1986; Low 1986). This process of CDR-grafting is a well established technique, but it has a downside in that it frequently generates an antibody with substantially decreased antigen binding affinity compared to the parental antibody. This decreased affinity is the result of unanticipated steric clashes between the human immunoglobulin framework and the murine CDR side chains, which alters the CDR loop conformation. This disadvantage can be overcome by the reiterative process of back-mutagenesis, which involves the restoration of key murine framework residues that are responsible for maintaining the correct CDR loop formations (Foote 1992). However, this process is laborious and random.

T84.66 is a murine monoclonal antibody with high specificity and affinity for carcinoembryonic antigen (CEA). CEA is one of the most well characterized human tumor-associated antigens (Wagener 1983). It is a glycoprotein that has limited expression in normal adults, and is commonly overexpressed in carcinomas of the colon, rectum, breast, lung, pancreas, and gastrointestinal tract (Marshall 2003). In fact, CEA is expressed on nearly 50% of all human tumors (Huang 2002). Increased CEA expression promotes intercellular adhesions, which may lead to metastasis (Marshall 2003).

T84.66 has an extensive clinical history, and has been used in the radioimmunotherapy treatment of over 200 patients. Radiolabeled murine T84.66 monoclonal antibody evaluated in the clinic is capable of imaging 69% of primary colorectal carcinomas prior to surgery (Beatty 1986), but it also generates a HAMA response (Morton 1988). The genes for the T84.66 antibody were cloned and a human-murine chimeric version (cT84.66) was expressed in mammalian cells (Neumaier 1990). In a pilot imaging study for colorectal disease using a single administration, only one out of 29 patients exhibited a human anti-chimeric antibody (HACA) response against cT84.66 (Wong 1997). However, as multiple administration immunotherapy trials have proceeded (Wong 1995; Wong 1999), an increase in the frequency of the HACA response has been noted. Thus, there is a need in the art for humanized T84.66 antibodies that maintain the high specificity and affinity of the parental antibody while minimizing the HAMA response.

SUMMARY OF THE INVENTION

In certain embodiments, the present invention discloses humanized antibodies that combine a binding site recognizing the same epitope as T84.66 and a polypeptide framework of a human or humanized antibody. In these embodiments, the antibodies may have a specific binding affinity ($K_A$) for CEA of at least about $1 \times 10^8$ $M^{-1}$. in certain embodiments, the antibodies may have a specific binding affinity ($K_A$) for CEA of at least about $1.1 \times 10^{10}$ $M^{-1}$ or at least about $1.9 \times 10^{10}$ $M^{-1}$. In certain embodiments, the variable light chain of the humanized antibodies may consist of the variable light chain of antibody 4D5, version 8 (Herceptin) (Eigenbrot 1993), wherein the L4, L24-L34, L50-L56, L66-L69, and L89-97 residues of Herceptin have been replaced with the corresponding residues from T84.66. In these embodiments, the variable light chain of the humanized antibodies may have the amino acid sequence of SEQ ID NO: 1. In some embodiments, the variable heavy chain of the humanized antibodies may consist of the variable heavy chain of Herceptin, wherein the H30-H35, H50-H58, and H93-H102 residues of Herceptin have been replaced with the corresponding residues from T84.66. In these embodiments, the variable heavy chain of the humanized antibodies may have the amino acid sequence of SEQ ID NO: 2. In other embodiments, the variable heavy chain of the humanized antibodies may consist of the variable heavy chain of Herceptin, wherein the H30-H35, H50-H65, H67, and H93-H102 residues of Herceptin have been replaced with the corresponding residues from T84.66. In these embodiments, the variable heavy chain of the humanized antibody may have the amino acid sequence of SEQ ID NO: 3. In certain embodiments, a conjugate such as a toxin, chemotherapeutic agent, radiolabel, or cytokine may be added to the humanized antibodies.

In another several embodiments, the present invention provides methods of detecting or localizing in a subject a tumor that expresses CEA by administering radiolabeled humanized antibodies that contain the antigen-binding site of T84.66 and a polypeptide framework of a human or humanized antibody and scanning the subject with a scanning device at some time period after administration.

In another several embodiments, the present invention provides methods of humanizing a non-human polypeptide donor molecule that contains a particular antigen-binding site by obtaining a first set of structural coordinates for the donor molecule, comparing the first set of structural coordinates to one or more sets of structural coordinates from potential human acceptor molecules, selecting an acceptor molecule based on a high degree of structural overlap with the donor molecule, superimposing the atomic molecular structures of the donor and acceptor molecules, identifying segments of the human acceptor molecule that differ from the donor molecule by visual inspection, and replacing the amino acid residues of these segments with the corresponding amino acid residues from the donor molecule. In certain embodiments, the donor and acceptor molecules may be antibodies.

In another several embodiments, the present invention provides a method of treating a subject having a tumor that expresses CEA by administering a humanized antibody containing the antigen-binding site of T84.66 and a polypeptide framework of a human or humanized antibody. In certain embodiments, the variable light chain of the humanized antibody may have the amino acid sequence of SEQ ID NO: 1. In some embodiments, the variable heavy chain of the humanized antibody may have the amino acid sequence of SEQ ID NO: 2, while in others it may have the amino acid sequence of SEQ ID NO: 3. In certain embodiments, a conjugate such as a radionuclide, toxin, cytokine, or chemotherapeutic agent may be attached to the humanized antibody.

In another several embodiments, the present invention provides a method of inhibiting the growth of a CEA-expressing tumor by administering a humanized antibody containing the antigen-binding site of T84.66 and a polypeptide framework of a human or humanized antibody. In certain embodiments, the variable light chain of the humanized antibody may have the amino acid sequence of SEQ ID NO: 1. In some embodiments, the variable heavy chain of the humanized antibody may have the amino acid sequence of SEQ ID NO: 2, while in others it may have the amino acid sequence of SEQ ID NO: 3. In certain embodiments, a conjugate such as a radionuclide, toxin, cytokine, or chemotherapeutic agent may be attached to the humanized antibody.

In another several embodiments, the present invention provides a vector that encodes the humanized variable light chain sequence of SEQ ID NO: 1. In certain embodiments, this vector may also encode the humanized variable heavy chain sequence of SEQ ID NO: 2 or SEQ ID NO: 3. In some embodiments, the vector may encode the amino acid sequence of the constant regions of one or more human or humanized immunoglobulin polypeptides.

In another embodiment, the present invention provides a cell line that expresses a humanized antibody containing the antigen-binding site of T84.66 and a polypeptide framework of a human or humanized antibody.

BRIEF DESCRIPTION OF THE DRAWINGS

FIG. 3: Structure-based sequence alignment of T84.66 variable light (VL, SEQ ID NO:28) and variable heavy (VH, SEQ ID NO:29) domains with Herceptin (VL, SEQ ID NO:30; VH, SEQ ID NO:31) M5A (VL, SEQ ID NO:1; VH, SEQ ID NO:2), and M5B (VL, SEQ ID NO:1; VH, SEQ ID NO:3). Peptide segments of human origin are shown in normal typeface. Peptide segments of murine origin are shown in bold typeface. Sequence numbers and CDR boundaries are according to Kabat. Note that the segments that were transplanted from donor to acceptor to create M5A and M5B do not necessarily correspond to Kabat CDRs.

DETAILED DESCRIPTION

Figure 1A:
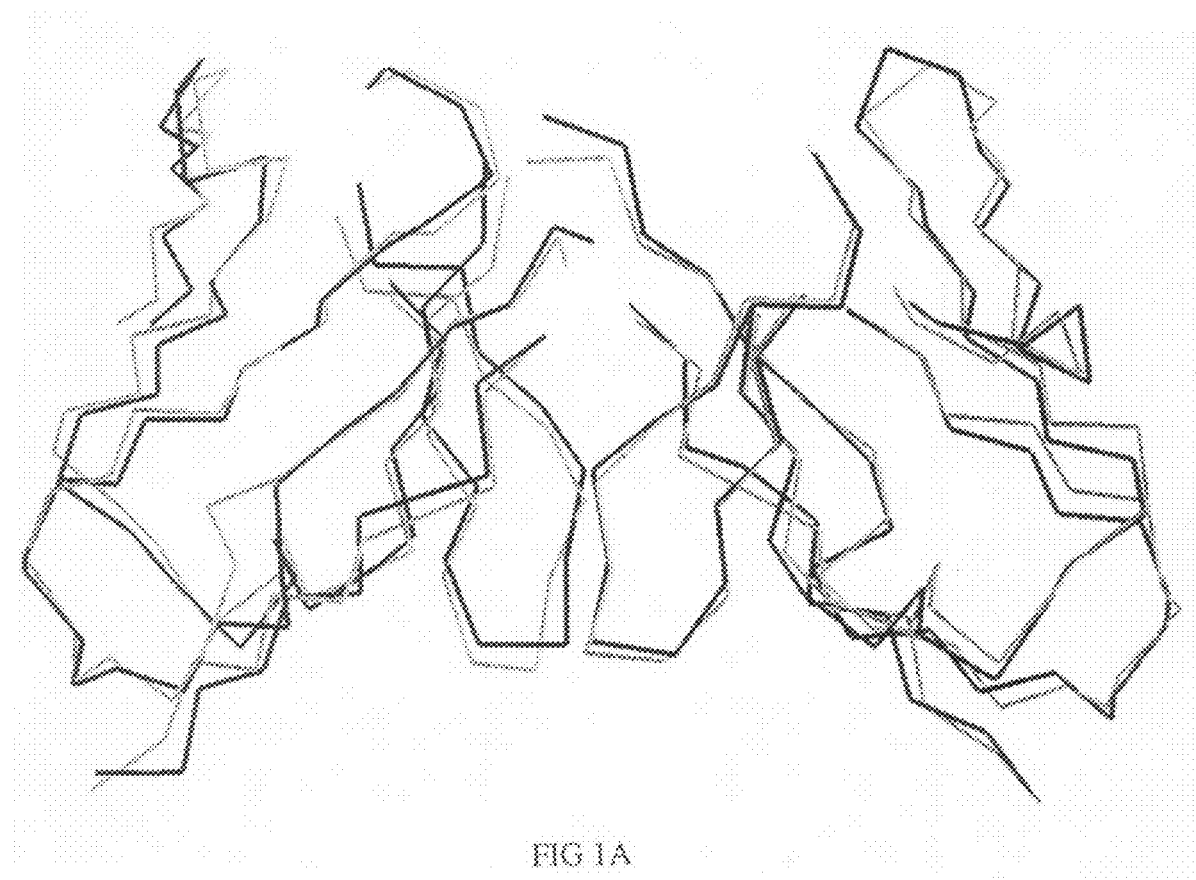
FIG. 1: Superimposed alpha carbon traces of T84.66 Fv (black) and Herceptin (gray). Two orthogonal views (A and B) are shown.

The high binding affinity and specificity of monoclonal antibodies to specific antigens makes them potentially powerful tools for the detection and treatment of a variety of diseases. Unfortunately, administration of a non-human monoclonal antibody to a human subject can result in the generation of a human antibody response, such as a HAMA or HACA response. Attempts to overcome this response have included the development of purely human antibodies and chimeric monoclonal antibodies. However, each of these solutions has resulted in certain drawbacks. More recently, humanized monoclonal antibodies have been created. These are similar to chimeric antibodies in that they contain a human constant region. However, unlike a chimeric antibody, the variable region of a humanized antibody is also primarily human. The only non-human portions of a humanized antibody are the CDR regions. In some humanized antibodies, additional human residues are added by substituting specific non-human residues within the CDR regions with their corresponding human residues.

The present invention is based on the development of a more efficient CDR grafting technique for the humanization of monoclonal antibodies. Crystallographic structural data has been utilized to select human acceptor molecules that have maximum structural overlap with the non-human donor molecule. This structural data has also been utilized to select which residues within the human acceptor molecule should be substituted with corresponding residues from the non-human donor molecule. Using this technique, a humanized version of the murine monoclonal antibody T84.66 has been created. In vitro, this humanized antibody exhibits levels of binding affinity and specificity for CEA that are nearly identical to those of the monoclonal antibody. Importantly, this humanized T84.66 has exhibited the ability to specifically target tumors that express CEA in vivo, making it a potentially powerful tool for the detection and treatment of such tumors.

As used herein, the term "antibody" refers to monoclonal antibodies, polyclonal antibodies, and antibodies prepared by recombinant nucleic acid techniques. The term may refer to an intact tetrameric immunoglobulin containing two complete light chains and two complete heavy chains, each with a variable region and a constant region. Alternatively, it may refer to a fragment thereof, such as an Fv fragment (containing only the variable regions of the light and heavy chains), an Fab fragment (containing the variable regions and some elements of the constant regions), a diabody, a single-chain antibody, or any other antibody fragment.

The term "humanized antibody" as used herein refers to an antibody containing structural elements of a human antibody (the acceptor) and the antigen binding site of a non-human antibody (the donor). "Humanized antibodies" contain a minimal number of residues from the non-human antibody. For instance, they may contain only the CDR regions of the non-human antibody, or only those residues that make up the hypervariable regions of the non-human antibody. They may also contain certain residues from outside the variable regions of the non-human polypeptide, such as residues that are necessary to mimic the structure of the non-human antibody or to minimize steric interference. In addition, humanized antibodies may contain residues that do not correspond to either the human or the non-human antibodies.

"Polypeptide" as used herein refers to any peptide or protein comprising two or more amino acids joined to each other by peptide bonds or modified peptide bonds, i.e., peptide isosteres. "Polypeptide" refers to both short chains, commonly referred to as peptides, oligopeptides, or oligomers, and to longer chains, generally referred to as proteins. Polypeptides may contain amino acids other than the gene-encoded amino acids. "Polypeptides" include amino acid sequences modified whether by natural processes, such as posttranslational processing, or by chemical modification techniques that are well known in the art. Such modifications are well describe in basic texts and in more detailed monographs, as well as in a voluminous research literature. Modifications can occur anywhere in a polypeptide, including the peptide backbone, the amino acid side-chains, and the amino or carboxyl termini. It will be appreciated that the same type of modification may be present in the same or varying degrees at several sites in a given polypeptide. Also, a single polypeptide may contain multiple modifications. Polypeptides may be branched as a result of ubiquitination, and they may be cyclic, with or without branching. Cyclic, branched, and branching cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or a nucleotide derivative, covalent attachment of a lipid or lipid derivative, covalent attachment of phosphotidylinositol, cross-linking, cyclization, disulfide bond formation, demethylation, formation of covalent cross links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for example, *Proteins—Structure and Molecular Properties, 2nd Ed.*, T. E. Creighton, W.H. Freeman and Company, New York, 1993; Wold, F., *"Posttranslational Protein Modifications: Perspectives and Prospects*, pgs. 1-12 in *Posttranslational Covalent Modification of Proteins"*, B. C. Johnson, Ed., Academic Press, New York, 1983; Seifter et al., *"Analysis for Protein Modifications and Nonprotein Cofactors ", Meth Enzymol* (1990) 182:626-646; and Rattan et al., *"Protein Synthesis: Posttranslational Modifications and Aging", Ann NY Acad Sci* (1992) 663:48-62.

"Structural coordinates" as used herein refers to the set of coordinates that describe the three-dimensional structure of a molecule, in particular a polypeptide or a fragment thereof. These coordinates may be derived from X-ray crystallographic or nuclear magnetic resonance studies. Structural coordinates may be obtained from any of a variety of available databases, such as the Protein Data Bank (Bernstein 1977; Berman 2000).

The term "acceptor" refers to a molecule that provides the structural framework for creation of a humanized molecule, such as a human immunoglobulin. The term "donor" refers to the molecule that provides the binding site element of a humanized molecule. This molecule is generally a non-human polypeptide, such as a murine monoclonal antibody.

"High degree of overlap" as used herein refers to the level of structural homology between a polypeptide acceptor molecule and a polypeptide donor molecule. Two molecules have a high degree of overlap when visual inspection of their overlayed three-dimensional structures reveals significant structural similarity.

"Vector" as used herein refers to a replicon such as a plasmid, phage, cosmid, or virus to which another nucleic acid segment may be operably inserted so as to bring about the replication or expression of that segment.

"Scanning device" as used herein refers to any device for detecting a radionuclide or fluorescent agent, such as a photoscanner for detecting radioactive activity. More specifically, "scanning device" refers to a device capable of detecting the presence of a radionuclide that has been injected in a subject, identifying the specific location of the radionuclide within the subject, and quantifying the amount of radionuclide within that specific location.

The term "treating" as used herein may refer to preventing a condition, slowing the onset or rate of development of a condition, reducing the risk of developing a condition, preventing or delaying the development of symptoms associated with a condition, reducing or ending symptoms associated with a condition, generating a complete or partial regression of a condition, or some combination thereof.

There are many examples in the published literature of antibody humanization via CDR-grafting (O'Brien 2003). However, this process often results in an antibody with substantially decreased binding affinity compared to the parental antibody. This decreased affinity is caused by unanticipated steric clashes between the human immunoglobulin framework and the mouse CDR residues, which alter the conformation of the antigen binding loops. Such steric clashes can be overcome by introducing back-mutations to restore key murine framework residues responsible for correct loop conformation, but this process is laborious and often reiterative (Foote 1992). The reason steric clashes in humanized antibodies have been unanticipated is because the constructs have been designed using molecular models of the graft donor and graft acceptor molecules, rather than actual crystal structures of those molecules. For instance, donor and acceptor molecules have previously been selected based on their amino acid sequences (Carter 2003; Pedersen 1997). In these approaches, the amino acid sequences of exposed regions of the murine antibody are obtained, and sequence databases are used to select a human antibody with the same or a similar sequence.

Recently, the crystal structure of the murine T84.66 variable region was solved by X-ray diffraction analysis of the T84.66 diabody (scFv dimer) to a resolution of 2.6 Å (Carmichael 2003). These data revealed several unusual structural features that had to be taken into consideration when designing the humanized T84.66 construct. CDR loops L2, L3, H1, and H2 had canonical structures as predicted from their sequences, but loops L1 and H3 were structurally unique. The 11-residue CDR-L1 loop resembled a canonical 13-residue loop, but the deletion of two residues from its tip caused an unpredicted twist in this region, as well as a disruption of the hydrogen bond network that stabilizes residues L30-L32. The structure of the 12-residue CDR-H3 loop was likewise not as predicted based on homologous structures, largely due to a rare proline residue located at position H94. Proline, lacking an amide hydrogen, is unable to participate in the hydrogen bonding network that normally stabilizes the base of most H3 loops and largely dictates their conformation (Morea 1998). To compensate, the proline participates in a hydrophobic cluster containing H27 (phe), H99 (val), H2 (val), H4 (leu), and the aromatic ring of H102 (tyr). This causes the tip of the anticipated CDR-H3 loop (H98-H100A) to fold over rather than extend toward the combining site as would be expected for a loop of this length.

Applicants have utilized T84.66 structural data in conjunction with structural data for the acceptor Fv (Herceptin) to generate a humanized T84.66 murine monoclonal antibody that requires no post-design back-mutagenesis to restore full antigen affinity. Selection of suitable VH and VL sequences based on structural data is superior to previous approaches that relied on sequence homology to select suitable VH and VL sequences (Johnson 2001; Pedersen 1997), because it assures that the selected VL:VH pair will have a domain pairing angle that matches that of T84.66. This match is important because it preserves the relative orientation of the heavy and light chain CDR loops. Knowing the crystal structure of both the graft donor and the graft acceptor removes the guesswork from determining which murine framework residues are necessary to preserve CDR loop conformation. The humanized antibody generated by this method retains the same high affinity for CEA as cT84.66, with essentially identical animal tumor targeting and biodistribution.

Molecular graphics technology was used to compare the X-ray coordinates of a single T84.66 Fv unit with those of human Fv units in the Protein Data Bank. Humanized antibody 4D5, version 8 (Herceptin) was selected as the most appropriate acceptor molecule for CDR grafting, based on a high degree of structural overlap and similarity of VL-VH domain pairing angles. Rather than transplanting the complete CDR regions of T84.66 into Herceptin, residues to be transplanted were selected based on structural compatibility. Visual inspection suggested that minimal disruption of the CDR loops could be achieved by substituting the L24-L34, L50-L56, L66-L69, L89-L97, H30-H35, H50-H58, and H93-H102 residues of Herceptin with the corresponding T84.66 residues. The resulting molecular model was inspected for potential steric clashes between donor and acceptor side chains. Based on this inspection, the L4 residue of Herceptin was replaced with the corresponding T84.66 residue. The resulting humanized antibody was dubbed M5A. Based on previous reports that failure to include residues H59-H65 in a humanized construct significantly reduced binding affinity, a second humanized antibody was created. This antibody, dubbed M5B, contained the same substitutions as M5A, but was further modified by replacing the H59-H65 and H67 residues of Herceptin with the corresponding T84.66 residues.

Fully synthetic genes encoding the VL chain and VH chains of M5A and M5B were created using splice overlap extension polymerase chain reaction. Purified full-length VL chain genes were ligated into the expression plasmid pEE12, while VH chain genes were ligated into the expression plasmid pEE6. Both of these plasmids had been previously modified to contain the cDNA sequence of the constant regions of a human $IgG_1$ antibody. The VH chain gene was then removed from pEE6 and ligated into the pEE12 VL chain plasmid. This dual chain pEE12/6 plasmid was electroporated into murine myeloma NS0 cells, and transfectants were screened using a recombinant CEA fragment-based ELISA. M5A and M5B antibodies were isolated and purified on a small scale.

Biochemical characterization was performed on purified aliquots of M5A, M5B, and cT84.66 antibodies. SDS-PAGE under reducing conditions revealed two bands corresponding to the light and heavy chain polypeptides. The M5A and M5B light chains had a slightly lower molecular weight than cT84.66. SDS-PAGE under non-reducing conditions and size-exclusion chromatography confirmed that the antibodies were assembled properly. M5A and M5B both displayed an isoelectric point different than that of cT84.66. The binding affinity of each antibody to CEA was determined by surface plasmon resonance. The affinity constants of each antibody were comparable ($K_A$=1.1×10$^{10}$ M$^{-1}$ for M5A, 1.9×10$^{10}$ M$^{-1}$ for M5B, and 1.6×10$^{10}$ M$^{-1}$ for cT84.66).

M5A, M5B, and cT84.66 were radiolabeled with $^{131}$I in preparation for tumor targeting studies. All three antibodies were highly immunoreactive to CEA in vitro. In vivo tumor targeting assays were carried out on athymic mice that had been subcutaneously injected with human colon carcinoma cells. After 10 days, the animals exhibited measurable tumor development. Radiolabeled antibodies were injected into the tail vein of each mouse, and at selected time points they were euthanized and their organs were counted for radioactivity. The level of M5A in tumor, blood, and other organs was not significantly different than that of cT84.66. M5B levels in blood and other organs was not significantly different than that of cT84.66, but M5B exhibited a lower overall tumor uptake.

M5A was selected for large-scale production based on its high tumor uptake and higher content of "human" residues. An M5A clone inoculated into a medium scale bioreactor generated a total antibody harvest of 640 mg over a 2-month period. This successful scale-up production of M5A illustrates the ability to generate sufficient amounts of the humanized antibodies of the present invention to conduct radioimmunotherapy trials. cT84.66 monoclonal antibody has already shown success in radioimmunotherapy, having been used to treat over 200 patients. M5A and M5B have both demonstrated the ability to bind CEA with a specificity and affinity similar to that of cT84.66, as well as the ability to target CEA-expressing tumors in vivo. In addition, they are less likely to trigger a host immune response than T84.66 or cT84.66, since they consist primarily of human residues. These characteristics make M5A and M5B ideal radioimmunotherapeutic agents.

In addition, as immunotherapy, antibodies with high specificity for tumor-associated antigens have been utilized in a variety of cancer therapies (Maynard 2000). Their high binding affinity and likely decreased host immune response makes the antibodies of the present invention ideal candidates for these therapies. The humanized antibodies of this invention may be conjugated with small molecule toxins, cytokines, or chemotherapeutic agents (e.g., doxurubicin) for specific delivery to cancer cells. In addition, binding of the humanized antibodies to tumor cells may be used to recruit host immune responses. This host immune response may be increased by utilizing bivalent antibodies, with one binding site corresponding to the humanized constructs of the present invention and another binding site that recognizes cytotoxic T-cells.

The humanized antibodies of the present invention may be administered for detection or localization of a tumor expressing CEA in a subject by subcutaneous, peritoneal, intravascular, intramuscular, intradermal or transdermal injection, among other methods. The antibodies may be labeled with a variety of labeling agents, including radioactive labels such as iodine ($^{123}$I, $^{124}$I, $^{125}$I, $^{131}$I), sulfur ($^{35}$S), tritium ($^{3}$H), indium ($^{111}$In, $^{112}$In), carbon ($^{14}$C), copper ($^{64}$Cu, $^{67}$Cu), yttrium ($^{86}$Y, $^{88}$Y, $^{90}$Y), lutitium ($^{177}$Lu), technicium ($^{99}$Tc, $^{99m}$Tc), rhenium ($^{186}$Re, $^{188}$Re), other lanthanides, luminescent labels, or fluorescent labels, or some combination thereof.

Antibodies against CEA have been used previously to treat tumors expressing CEA in mice (Imikare 2004; Blumenthal 2005). Humanized antibodies of the present invention may be administered to treat a subject having a tumor expressing CEA or to inhibit the growth of a tumor expressing CEA using any of the administration routes discussed above for the detection of tumors. Humanized antibodies may be labeled as described above, or they may be unlabeled. In addition, the humanized antibodies may be associated with a conjugate. Those of skill in the art will recognize that a variety of conjugates may be coupled to the humanized antibodies (see, for example, "Conjugate Vaccines", Contributions to Microbiology and Immunology, J. M. Cruse and R. E. Lewis, Jr. (eds.), Carger Press, New York, (1989)). These conjugates may be linked to the humanized antibodies by covalent binding, affinity binding, intercalation, coordinate binding, or complexation, among other methods. Conjugates may also consist of chemotherapeutic agents such as vindesine, cisplatin, doxurubicin, or adriamycin, or any other compound useful in the treatment of cancer, or toxins such as ricin or diptheria toxin, among others. In addition, various drugs and therapeutic agents that are not conjugated to the antibodies may be administered in conjunction with the antibodies.

For detection and localization of tumors expressing CEA, the humanized antibodies of the invention may be administered at a dose sufficient for detection by a scanning device. This dosage will be dependent on the type of label being used. The type of scanning device to be used will vary depending on the label being used, and one skilled in the art will easily be able to determine the appropriate device. For treating a subject having a tumor expressing CEA, or for inhibiting the growth of a tumor expressing CEA, the humanized antibodies of the invention may be administered in a therapeutically effective amount. A therapeutically effective amount as used herein refers to that amount that produces a desired therapeutic effect in a subject. The precise therapeutically effective amount is an amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy $20^{th}$ Edition, Gennaro, Ed., Williams & Wilkins Pennsylvania, 2000.

For detection or treatment of a tumor expressing CEA, the humanized antibodies of the present invention may be prepared as a formulation within pharmaceutically acceptable media. This formulation may include physiologically tolerable liquids, gels, solid carriers, diluents, adjuvants, or excipients, or some combination thereof. The pharmaceutical formulation containing the humanized antibody may be administered alone or in combination with other known tumor therapies. Effective dosage will depend in part on the weight, age, and state of health of the subject, as well as the administration route and extent of tumor development.

The humanized antibodies of the present invention or portions thereof may be expressed using any appropriate expression system. Nucleic acid sequences encoding variable light (VL) and variable heavy (VH) chains of a particular humanized antibody may be expressed using separate vectors, or both chains may be expressed from one vector. A nucleotide sequence encoding the VL chain, the VH chain, or both chains together may be inserted into a suitable vector. The vector may contain a variety of regulatory sequences, such as promoters, enhancers, or transcription initiation sequences, as well as genes encoding markers for phenotypic selection. Such additional sequences are well known in the art. The vector may be selected from the group consisting of, but not limited to, plasmid, cosmid, lambda phage, M13 phage, retrovirus, lentivirus, adenovirus, herpes simplex virus (HSV), cytomegalovirus (CMV), adeno-associated virus (AAV), papillomavirus, and simian virus 40 (SV40). Additionally, the vector may contain a nucleotide sequence encoding the constant heavy (CH) and constant light (CH) chains of a human immunoglobulin. Alternatively, the vector may express only the VH and VL chains of a particular humanized antibody, with the expressed polypeptide comprising an Fv fragment rather than a whole antibody. The host cell may be selected from a variety of cell types, including for example bacterial cells such as *E. coli* or *B. subtilis* cells, fungal cells such as yeast cells or *Aspergillus* cells, insect cells such as *Drosophila* S2 or *Spodoptera* Sf9 cells, or animal cells such as fibroblasts, CHO cells, COS cells, NSO cells, HeLa cells, BHK cells, HEK 293 cells, or human cells. Preferably, a mammalian cell type is utilized.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLE 1

Humanization of T84.66 Monoclonal Antibody

Figure 1B:
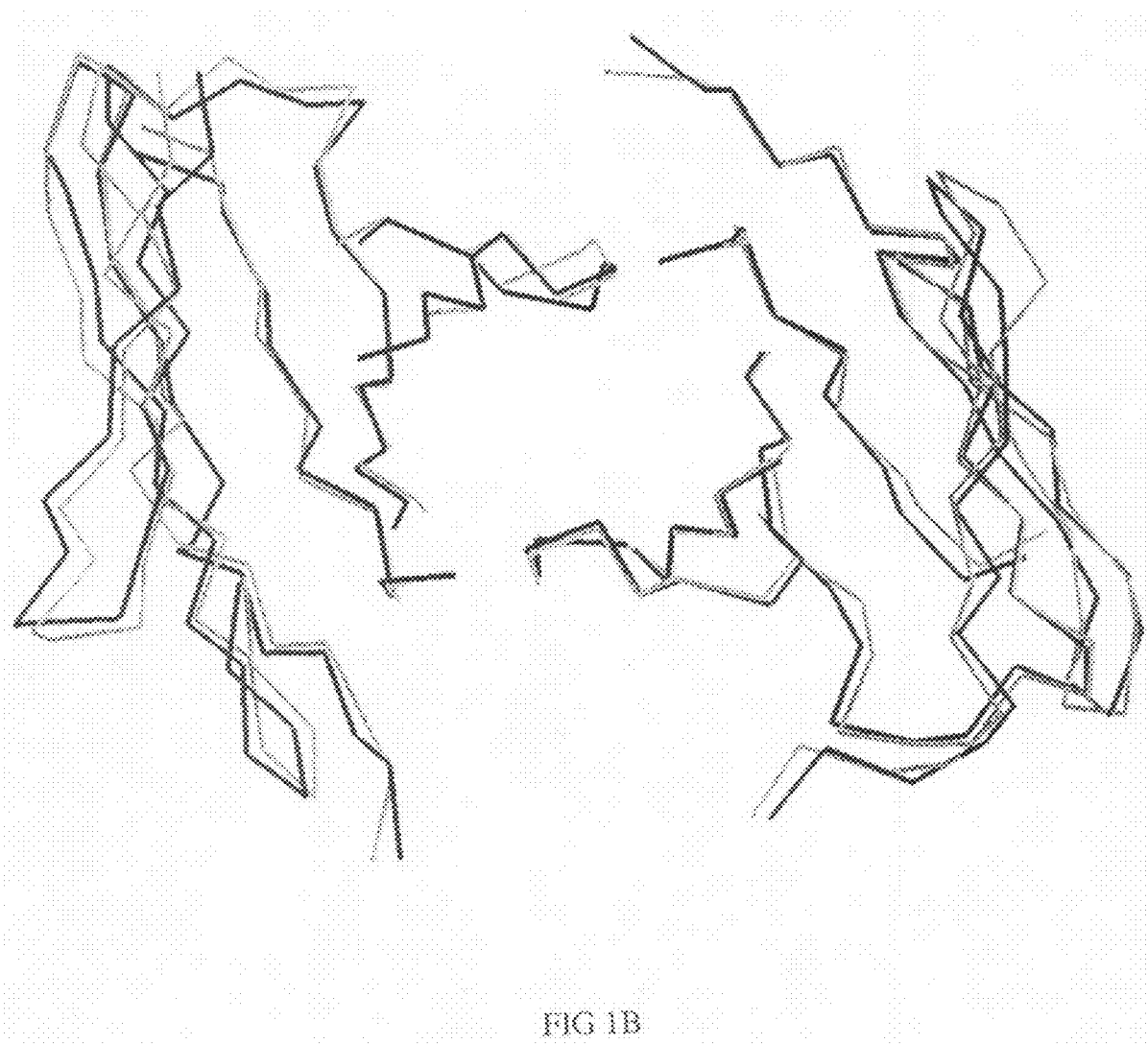

Using molecular graphics technology, X-ray coordinates for a single T84.66 Fv unit were extracted from the coordinate set of the corresponding diabody structure (PDB file 1 MOE). The T84.66 Fv coordinate set was then submitted to VAST, a web-based least-squares structural alignment server (Gibrat 1996), in order to identify a human or humanized Fv in the Protein Data Bank (Bernstein 1977; Berman 2000) whose framework would serve as a suitable acceptor for the proposed CDR graft. Of the antibodies that appeared in the list of homologous structures, humanized antibody 4D5, version 8 (anti-p185$^{HER2}$, Herceptin, PDB file 1 FVC) (Eigenbrot 1993) was selected as the most appropriate framework provider for the proposed CDR graft, because the degree of overlap (root-mean-square deviation of 1.07 Å for 1,326 backbone atoms) was high and the angle of VL-VH domain pairing was essentially the same (FIGS. 1A, 1B). The amino acid sequence of the T84.66 variable light and variable heavy chains are shown in SEQ ID NOs: 4 and 5, respectively. The amino acid sequence of the Herceptin light and variable heavy chains are shown in SEQ ID NOs: 6 and 7, respectively.

Analysis of the structural data for Herceptin (as an Fv, determined to a resolution of 2.2 Å) (Carter 1992, Eigenbrot 1993) confirmed the influence of certain framework residues on CDR loop conformation. Specifically, it identified framework residues L66, H71, and H93 as major CDR loop conformation determinants (CDR-L1, H2, and H3, respectively). Of particular interest was the arginine at L66, which formed a salt bridge with the aspartate at L28 in CDR-L1. Mutation of L66 results in a four-fold decrease in antigen affinity, suggesting that the residue may interact with antigen. The structural roles played by residues L55, H73, H78, and H102, and the effects of mutating each, were also evaluated.

Upon superimposing the T84.66 donor Fv and Herceptin acceptor Fv structures, it became clear that the peptide segments that needed to be transplanted did not necessarily correspond to the complementarity determining regions (CDRs) defined by Kabat (Wu 1970) or Chothia (Chothia 1987) or the specificity determining regions (SDRs) defined by Padlan (Padlan 1995). Rather, the segments simply corresponded to regions that differed in structure when the two Fv units were superimposed. Visual inspection of the superimposed structures suggested that minimal disruption of the CDR loops could be achieved by deleting seven peptide segments (L24-L34, L50-L56, L66-L69, L89-L97, H30-H35, H50-H58, H93-H102) from the Herceptin acceptor Fv and replacing them with corresponding segments from the T84.66 donor Fv. In constructing the hybrid VL chain, a non-CDR peptide segment L66-L69 from T84.66 was transplanted onto the Herceptin acceptor because residue L66 was shown to influence the conformation of Herceptin CDR-L1, as described above. In constructing the hybrid VH, all three CDR boundaries were altered. The Kabat definition of CDR-H1 (H31-H35) was expanded to include H30, since this residue packs against the tip of CDR-H2 in T84.66. In addition, based on our knowledge of the key structural role played by the rare proline at position H94 in T84.66, we expanded the Kabat definition of CDR-H3 to include framework residues H93 and H94. The importance of residue H93 has been noted by others (Xiang 1995).

Figure 2A:
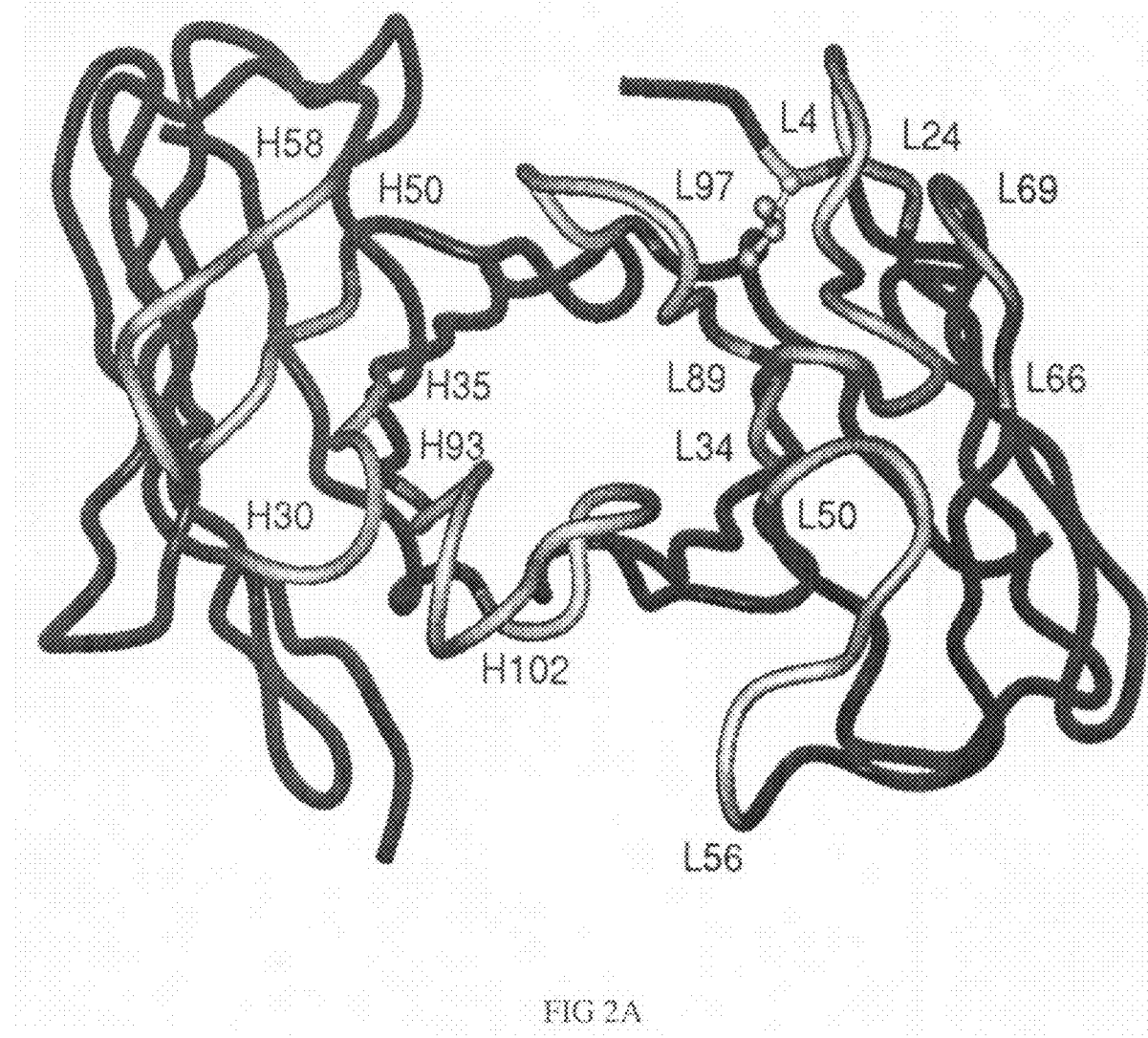
FIG. 2: A. Ribbon rendering of humanized T84.66 antibody M5A. B. Ribbon rendering of humanized T84.66 antibody M5B. Black segments represent human residues from Herceptin. White segments represent murine residues from T84.66. Segment boundaries are labeled with residue numbers. Residues rendered in ball-and-stick are framework residues that were back mutated to alleviate steric clashes with adjacent CDR residues.

Upon completing the graft, the resulting molecular model was inspected for potential steric clashes between donor and acceptor side chains at the CDR-framework interface. A single clash between framework residue L4 (met) and CDR-L1 residue L33 (leu) was alleviated by replacing the former with its murine equivalent (leu). The resulting humanized construct, dubbed M5A (FIG. 2a), was subjected to an energy minimization algorithm (conjugate gradients to a maximum derivative of 5.0 kcal/mol-Å) to optimize bond lengths and angles at the splice junctions.

Figure 2B:
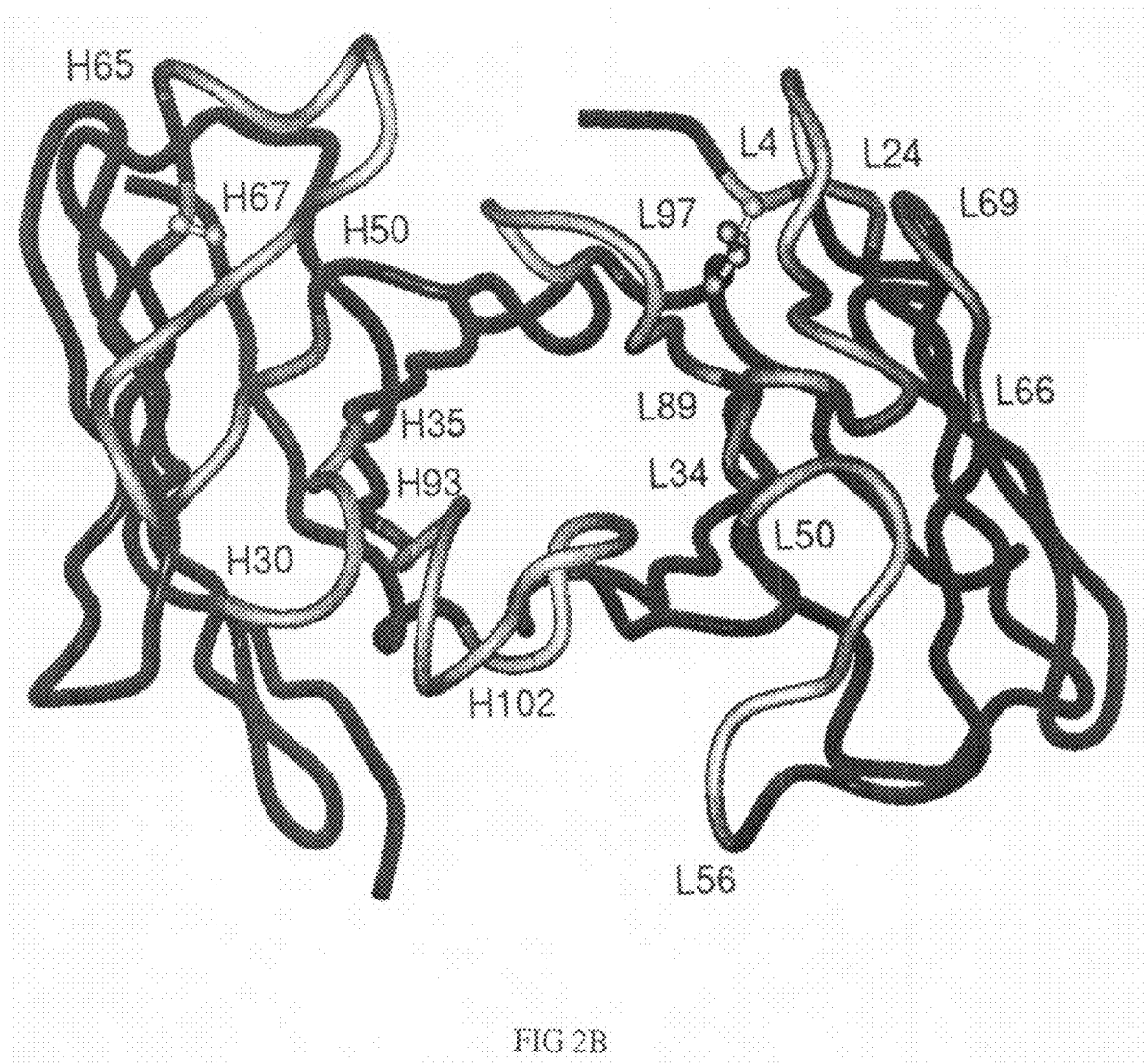

For CDR-H2, there is a wide discrepancy between Kabat's definition based on sequence hypervariability (H50-H65) and Chothia's definition based on structural variability (H52-H56). To further complicate matters, only residues H50-H58 of Kabat CDR-H2 interact with antigen in cases where antibody-antigen co-crystals have been examined (Padlan 1995; MacCallum 1996). However, two independent humanization reports suggest that this is not always the case, since failure to include murine residues H59-H65 in the humanized construct reduced binding affinity over 1000-fold in each case (Eigenbrot 1994; O'Connor 1998). For this reason, a second humanized construct, M5B, was created (FIG. 2b). In M5B, the H59-H65 peptide segment from Herceptin has been deleted and replaced with the corresponding segment from T84.66, so that the resultant construct contains the entire Kabat CDR-H2 loop from T84.66. To accommodate the additional segment, framework residue H67 (phe) was replaced with its murine equivalent (ala) to alleviate a steric clash with CDR-H2 residue H63 (phe). The amino acid sequence of the VL chain of M5A and M5B is shown in SEQ ID NO: 1. The amino acid sequence of the VH chains of M5A and M5B are shown in SEQ ID NOs: 2 and 3, respectively. The structure-based sequence alignment of T84.66 variable light (VL) and variable heavy (VH) domains with Herceptin, M5A, and M5B is shown in FIG. 3.

EXAMPLE 2

Generation of Synthetic Genes Encoding Humanized T84.66

Splice overlap extension polymerase chain reaction (SOE-PCR) (Horton 1989) was used to create fully synthetic genes encoding the M5A and M5B immunoglobulin variable region (Fv) genes. Eight oligonucleotides (Integrated DNA Technologies, Inc., Coralville, Iowa) ranging in size from 79 to 89 bases were required for each domain construct. The degree of overlap between adjacent oligonucleotides corresponded to 30 base pairs. The PCR primer sequences for the variable light (VL) and variable heavy (VH) domains are shown in SEQ ID NOs: 8-24.

Four SOE-PCR amplifications were required to build each variable domain gene. The internal-most pair of primers (4 and 5) were amplified first. The resulting PCR product was gel purified and further extended with the next set of external primers (3 and 6). The third extension utilized primers 2 and 7, and the final extension utilized primers 1 and 8. Each 50 µL reaction contained reaction buffer, 2 units of Vent DNA Polymerase (New England Biolabs, Beverly, Mass.), amplification primers at 1 µM each, and dNTPs at 200 µM. Using a GeneAmp PCR 9600 thermocycler (Perkins Elmer, Wellesley, Mass.), samples were heated for 2 min at 94° C., followed by 30 cycles of heating for 30 sec at 94° C., 30 sec at 55° C., and 30 sec at 72° C. After 30 cycles, the temperature was held constant at 72° C. for 10 min to ensure complete extension. In each case, the completed PCR reaction mix was electrophoresed on a 1% agarose gel (Sigma Chemicals, St. Louis, Mo.), and the desired product extracted from a 200 mg gel slice using a Qiaquick column (Qiagen, Valencia, Calif.). The coding region of the synthetic gene encoding the M5A/M5B VL chain is shown in SEQ ID NO: 25. The coding regions of the synthetic genes encoding the M5A VH chain and the M5B VH chain are shown in SEQ ID NOs: 26 and 27, respectively. For the second, third, and fourth reactions, 10 ng of purified product from the preceding reaction was used as the template. Individually, the purified full-length synthetic genes were digested with Xba I and Xho I and ligated into one of two expression plasmids (pEE12 for VL; pEE6 for VH). These plasmids, which contain the Glutamine Synthetase (GS) gene (Lonza Biologics, Slough, UK; Bebbington 1992) had been previously modified to contain the cDNA corresponding to the constant regions of a human $IgG_1$ antibody. In the pEE12 light chain plasmid, residue L104, whose codon is part of the Xho I restriction site, was mutated from leucine to valine using a Quik-Change kit (Stratagene, San Diego, Calif.) in order to restore the Herceptin sequence in this region. A dual chain plasmid was constructed by digesting the pEE6 heavy chain plasmid with BglII and Bam HI to isolate the heavy chain gene, which was then ligated into the BamHI site of the pEE12 light chain plasmid. The entire $IgG_1$ gene was sequenced in both directions to confirm its identity. Prior to electroporation, the dual chain plasmid was linearized with Sal I, filtered through a protein binding membrane to remove the restriction enzyme (Millipore, Bedford, Mass.), ethanol precipitated, and resuspended in sterile water to a concentration of 1 µg/µl.

EXAMPLE 3

Expression and Purification of Humanized T84.66

The dual chain pEE12/6 expression vector was electroporated into murine myeloma NS0 cells following procedures as previously described (Bebbington 1992; Yazaki 2001). Selection of transfectants in glutamine-free culture media (JRH Biosciences, Kenexa, Ky.) resulted in numerous clones, which were screened using a recombinant CEA fragment (Young 1998) based ELISA (Yazaki 2001).

Individually, the cell culture harvests were clarified by batch treatment (5% w/v) with the anion exchanger, AG1x8 (Bio-Rad Laboratories, Hercules, Calif.). The initial small-scale purification was on a Protein A column (Procept A; Millipore, Bedford, Mass.; 0.46 cm d, 10 cm h, 2.5 ml/min) pre-equilibrated with phosphate buffered saline (PBS). The clarified harvest was loaded and washed with 20 mM sodium phosphate pH 7.4, 20 mM sodium citrate, and 0.5 M NaCl. The antibodies eluted with 10 mM sodium phosphate, pH 4.0. The Protein A eluted peak was dialyzed vs. 50 mM sodium phosphate pH 5.5 prior to loading on a cation exchange column (Source 15S, Amersham Pharmacia Biotech, 2 ml/min, 0.4 cm d, 10 cm h). The antibodies were eluted with a linear gradient from 0 to 0.4 M NaCl/50 mM sodium phosphate pH 5.5. The eluted material was collected in tubes containing 1 M Tris, pH 8 (10% v/v). Assayed by SDS-PAGE and HPLC size exclusion, the antibody-containing fractions were pooled and dialyzed overnight vs. PBS and analyzed.

EXAMPLE 4

Biochemical Characterization of Humanized T84.66

Antibody quantitation was done on a Protein A affinity column (Amersham Pharmacia Biotech; 0.46 cm id×10 cm h, 0.5 ml/min). The column was equilibrated in PBS, sample loaded, washed with 20 mM sodium phosphate pH 7.4/20 mM sodium citrate/0.5 M NaCl, and eluted with a gradient from 0.1 M sodium citrate to 0.1 M citric acid. Absorbance was monitored at 280 nm, and the peak height of the antibody calculated based on a cT84.66 standard.

Figure 4A:
FIG. 4: A. Aliquots of purified M5A, M5B, and cT84.66 antibodies along with protein standards were electrophoresed under both non-reducing (three lanes adjacent to standard) and reducing (three right lanes) conditions by SDS-PAGE. Proteins were detected by Coomassie Brilliant Blue R-250 staining. B. Size-exclusion chromatography was carried out on a Superdex 200 HR 10/30 column.

Aliquots of purified M5A, M5B and cT84.66 antibodies, along with Kaleidoscope protein standards (Bio-Rad Laboratories), were electrophoresed under non-reducing and reducing conditions by SDS-PAGE (Laemmli 1970) on pre-cast 10% polyacrylamide Ready Gels (Bio-Rad Laboratories). Proteins were detected by Coomassie Brilliant Blue R-250 staining. SDS-PAGE under reducing conditions revealed two bands corresponding to the light (25 kDa) and heavy (50 kDa) chain polypeptide, with the M5A and M5B kappa light chain having a slightly lower molecular weight as compared to cT84.66 (FIG. 4a). SDS-PAGE under non-reducing conditions confirmed proper antibody assembly (FIG. 4a).

Figure 4B:
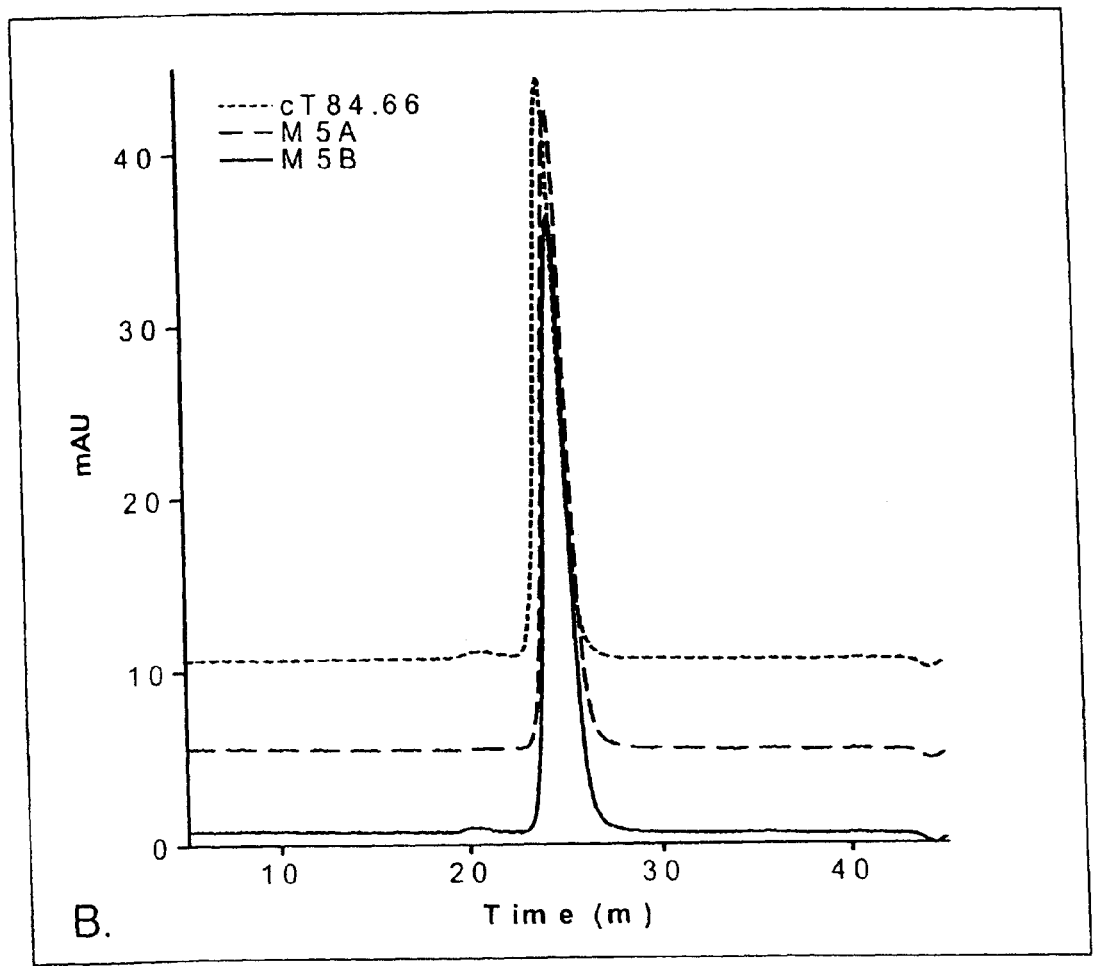

Size-exclusion chromatography was carried out on a Superdex 200 HR10/30 column (Amersham Pharmacia Biotech, 0.5 ml/min), run isocratic with PBS. The column was standardized using a gel filtration standard (Bio-Rad laboratories). A single peak corresponding to a molecular weight of 150 kDa confirmed proper antibody assembly (FIG. 4b).

Figure 5:
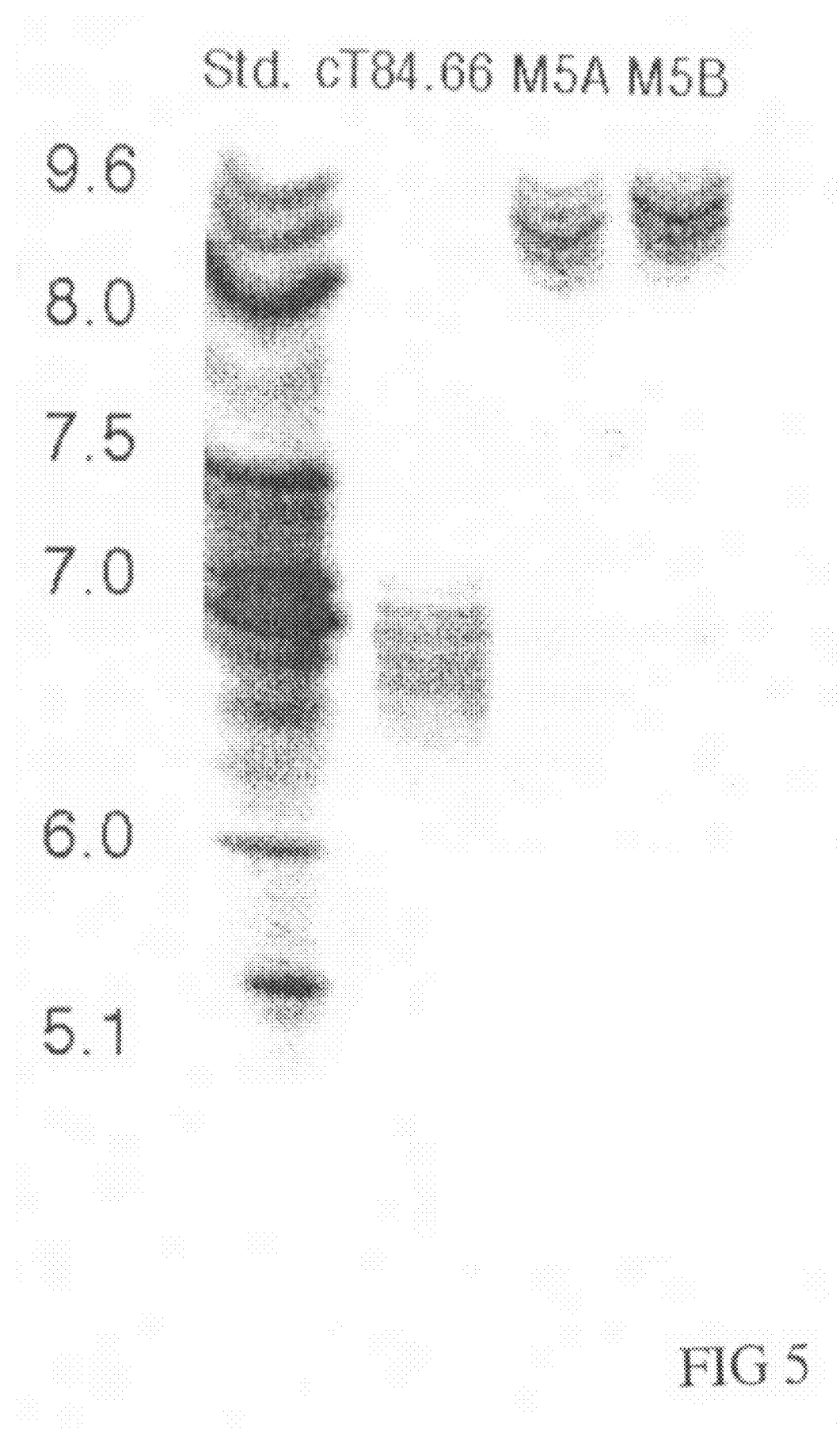
FIG. 5: IEF gel. Aliquots of the purified M5A, M5B, and cT84.66 antibodies along with protein standards were electrophoresed on isoelectric focusing gels.

The isoelectric point of the antibodies was determined on pH 4-7 IEF gels (Novex Inc, San Diego, Calif.) compared with IEF standards (Bio-Rad Laboratories). Both M5A and M5B showed a distinct isoelectric point (pI) difference from parental T84.66 monoclonal antibody (FIG. 5).

The binding affinity of the antibodies to purified CEA was determined by surface plasmon resonance (SPR) on a Biacore 1000 (Biacore AB, Uppsala, SW). CEA was biotinylated using the EZ-Link Sulfo-NHS-LC-Biotin kit (Pierce, Rockford, Ill.) and immobilized to a SA biosensor chip (Biacore Inc.) in HBS buffer. A series of increasing antibody concentrations (3.12, 6.25, 12.5, 25, 50, and 100 nM) were injected over a low density (175 $R^U$) of the immobilized CEA-biotin for the association and dissociation phase, with regeneration by a single pulse of 6 M GuHCl. The data were analyzed by BIAevaluation (v3.0) software using the bivalent analyte model to calculate the $K_A=k_{on}/k_{off}$. Antibody concentrations were determined by amino acid analysis. The affinity constants ($K_A$) of the M5A, M5B, and cT84.66 antibodies to CEA were $1.1\times10^{10} M^{-1}$, $1.9\times10^{10} M^{-1}$, and $1.6\times10^{10} M^{-1}$, respectively, demonstrating comparable binding for each antibody. Results of binding affinity assays are summarized in the following table:

| Antibody | $k_{on}$ (1/mol·s) | $k_{off}$ (1/s) | $K_A = k_{on}/k_{off}$ |
|---|---|---|---|
| M5A | $3.3 \times 10^5$ | $3.01 \times 10^{-5}$ | $1.1 \times 10^{10}$ M$^{-1}$ |
| M5B | $4.88 \times 10^5$ | $2.56 \times 10^{-5}$ | $1.9 \times 10^{10}$ M$^{-1}$ |
| cT84.66 | $2.61 \times 10^5$ | $1.62 \times 10^{-5}$ | $1.6 \times 10^{10}$ M$^{-1}$ |

EXAMPLE 5

Tumor Targeting using Humanized T84.66

M5A, M5B, and cT84.66 were radiolabeled with $^{131}$I by the Iodogen method as previously described (Wu 1996). Radiolabeling efficiency was determined by integrating peaks of the radiochromatograms from tandem Superose 6 HR 10/30 size exclusion columns (Amersham Pharmacia Biotech) and determining the percentage of radioactivity associated in the 160 kDa antibody peak. Each of the antibodies exhibited 100% incorporation of the radiolabel. Immunoreactivity was determined by in vitro incubation of each labeled antibody with a 20-fold excess (w/w) of purified CEA in PBS/1% human serum albumin (HASA), followed by size exclusion HPLC analysis to measure the formation of antibody:antigen complexes. All three antibodies were highly immunoreactive to CEA.

To determine the in vivo tumor targeting capability of M5A and M5B, applicants conducted animal biodistribution in tumor bearing animals. Groups of 7-to 8-week old female athymic mice (Charles River Laboratories, Wilmington, Mass.) were injected subcutaneously in the flank region with 106 LS174T human colon carcinoma cells obtained from American Tissue Culture Center (ATCC, Manassas, Va.). After 10 days, when tumor masses were in the range of 100-300 mg, one to three microcuries (μCi) per animal (2-3 μg of antibody) of $^{131}$I-M5A, M5B, or cT84.66 antibody were injected into the tail vein. At selected time points (0, 6, 24, 48, 72, and 96 h), groups of five mice were euthanized, necropsy was performed, and their organs were weighed and counted for radioactivity. All data are mean values, and have been corrected for radiodecay back to the time of injection. This allows organ uptake to be reported as "percent of the injected dose per gram" (% ID/g) with standard errors. Blood curves were calculated using ADAPT II software (D'Argenio 1979).

To compare changes in percent of the injected dose per gram over time between the M5A, M5B, and cT84.66 antibodies, two-way analysis of variance (ANOVA) was performed (D'Argenio 1979). The interaction between time and antibody level was included in the statistical model. Dependant variables compared using this model included the percent injected dose per gram for blood, liver, spleen, kidney, lung, tumor, and carcasses. Tumor-to-blood ratios and tumor masses were recorded. To compare differences between the antibodies at specific time points, the independent t-test was used. All significance testing was done at the 0.01 level, using SAS/STAT software (SAS Inc., Cary, N.C.). Results of biodistribution assays for each of the three antibodies are summarized in the following table (standard deviations in parentheses):

| | Time (hours) | | | | | |
|---|---|---|---|---|---|---|
| | 0 | 6 | 24 | 48 | 72 | 96 |
| cT84.66 mAb | | | | | | |
| Blood | 31.75 | 17.89 | 13.47 | 6.67 | 6.30 | 5.19 |
| | (1.36) | (1.04) | (0.88) | (1.11) | (0.50) | (0.72) |
| Liver | 6.22 | 4.11 | 2.87 | 2.00 | 1.68 | 1.51 |
| | (0.47) | (0.30) | (0.29) | (0.16) | (0.14) | (0.18) |
| Spleen | 4.66 | 3.60 | 2.78 | 1.60 | 1.57 | 1.31 |
| | (0.35) | (0.27) | (0.28) | (0.15) | (0.15) | (0.21) |
| Kidney | 5.24 | 3.56 | 2.77 | 1.67 | 1.34 | 1.15 |
| | (0.39) | (0.29) | (0.18) | (0.29) | (0.16) | (0.18) |
| Lung | 8.05 | 6.13 | 4.68 | 2.65 | 2.43 | 1.92 |
| | (0.56) | (0.41) | (0.27) | (0.50) | (0.16) | (0.23) |
| Tumor | 1.05 | 13.53 | 24.11 | 24.08 | 25.31 | 25.45 |
| | (0.09) | (1.26) | (0.94) | (3.75) | (2.38) | (3.04) |
| Carcass | 2.04 | 3.25 | 2.95 | 2.02 | 1.80 | 1.53 |
| | (0.04) | (0.22) | (0.08) | (0.24) | (0.10) | (0.17) |
| M5A mAb | | | | | | |
| Blood | 38.7 | 23.86 | 11.92 | 10.31 | 5.10 | 3.75 |
| | (0.65) | (0.79) | (0.72) | (1.15) | (0.68) | (0.39) |
| Liver | 8.14 | 5.42 | 2.44 | 2.65 | 1.68 | 1.27 |
| | (0.48) | (0.30) | (0.29) | (0.11) | (0.37) | (0.18) |
| Spleen | 7.35 | 4.63 | 2.35 | 2.67 | 1.52 | 1.05 |
| | (0.65) | (0.43) | (0.28) | (0.34) | (0.31) | (0.23) |
| Kidney | 6.75 | 4.80 | 2.43 | 2.27 | 1.20 | 0.90 |
| | (0.11) | (0.21) | (0.31) | (0.17) | (0.28) | (0.21) |
| Lung | 11.09 | 7.84 | 4.18 | 3.59 | 2.00 | 1.45 |
| | (0.72) | (0.15) | (0.41) | (0.26) | (0.43) | (0.37) |
| Tumor | 1.78 | 14.06 | 26.83 | 32.65 | 22.67 | 23.83 |
| | (0.09) | (1.26) | (0.94) | (3.75) | (2.38) | (3.04) |
| Carcass | 2.5 | 3.44 | 2.75 | 2.67 | 1.68 | 1.39 |
| | (0.12) | (0.05) | (0.20) | (0.13) | (0.21) | (0.18) |
| M5B mAb | | | | | | |
| Blood | 31.37 | 15.81 | 10.49 | 8.43 | 5.79 | 5.81 |
| | (1.00) | (0.43) | (0.51) | (0.92) | (0.83) | (0.63) |
| Liver | 8.2 | 3.54 | 3.06 | 2.31 | 1.72 | 1.72 |
| | (0.41) | (0.11) | (0.33) | (0.10) | (0.19) | (0.15) |
| Spleen | 5.53 | 3.31 | 2.51 | 2.07 | 1.53 | 1.83 |
| | (0.30) | (0.26) | (0.22) | (0.11) | (0.17) | (0.33) |
| Kidney | 5.13 | 3.17 | 2.43 | 2.01 | 1.38 | 1.52 |
| | (0.51) | (0.15) | (0.28) | (0.22) | (0.20) | (0.15) |
| Lung | 9.51 | 5.05 | 3.74 | 3.35 | 2.41 | 2.30 |
| | (0.68) | (0.16) | (0.15) | (0.27) | (0.41) | (0.16) |
| Tumor | 5.17 | 10.52 | 19.58 | 24.83 | 18.57 | 17.15 |
| | (3.66) | (0.75) | (0.92) | (4.84) | (2.62) | (2.25) |
| Carcass | 2.36 | 2.56 | 2.54 | 2.18 | 1.81 | 1.60 |
| | (0.18) | (0.10) | (0.10) | (0.10) | (0.14) | (0.10) |

These results showed that M5A antibody levels in blood, tumor, and other organs were not significantly different than those for cT84.66 antibody. M5B antibody levels were also not significantly different than cT84.66 antibody levels in blood or any other organ, but M5B had a lower overall uptake in the tumor (p=0.0116).

EXAMPLE 6

Large-scale Production of Humanized T84.66

M5A was selected over M5B for large-scale production based on its higher tumor uptake and higher content of "human" residues. The best producing M5A clone was inoculated into a medium scale Cell Pharm (CP) 2000 hollow fiber bioreactor according to the operator's manual (Biovest International, Minneapolis, Minn.) to determine production capabilities and to produce material for protein scale-up. The CP2000 was equipped with a single 20 sq. ft. hollow fiber cartridge (mw exclusion 10 kDa) and 10 sq. ft. oxygenator. The pH, glucose, lactate, ammonia, and antibody production levels were monitored every other day. Adjustments were made to the incoming $O_2$ and $CO_2$ levels to maintain pH between 7-7.2. Twenty liter bags of IMDM media (Biowhittaker, Walkerville, Md.) supplemented with 2% FBS (Hyclone, Logan, Utah) were used in the intracapillary space (ICS). Selective GS media (JRH Bioscience, Lenexa, Kans.)+2% FBS was used in the extracapillary space (ECS). The ICS feed rate was 1.2-2 L/day and the recirculation rate was 350-500 ml/min. An Autoharvester (Biovest International) was connected to the ECS and ran at a feed rate of 30-80 ml per day during the production run. Anti-CEA activity levels reached over 250 μg/ml, resulting in a total antibody harvest of 640 mg during a 2-month period.

As stated above, the foregoing are merely intended to illustrate the various embodiments of the present invention. As such, the specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Beatty, J. D., et al. 1986. Pre-operative imaging of colorectal carcinomas with 111 In-labeled anti-carcinoma antigen monoclonal antibody. Cancer Res 46:6494-6502.
2. Bebbington, C., et al. 1992. High-level expression of a recombinant antibody from myeloma cells using a glutamine synthetase gene as an amplifiable selection marker. Biotechnology 10:169-175.
3. Berman, H. M., et al. 2000. The Protein Data Bank. Nucleic Acids Res 28:235-242.
4. Bernstein, F., et al. 1977. The Protein Data Bank: a computer-based archival file for macromolecular structures. J Mol Biol 112:535-542.
5. Blumenthal, R. D., et al. 2005. Carcinoembryonic antigen antibody inhibits lung metastasis and augments chemotherapy in a human colonic carcinoma xenograft. Cancer Immunol Immunother 54:315-327.
6. Bruggemann, M., et al. 1991. Human antibody production in transgenic mice: expression from 100 kb of the human IgH locus. Eur J Immunol 21:1323-1326.
7. Carmichael, J. A., et al. 2003. The crystal structure of an anti-CEA scFv diabody assembled from T84.66 scFvs in V(L)-to-V(H) orientation: implications for diabody flexibility. J Mol Biol 326:341-351.
8. Carter, P. J., et al. 2003. Method for making humanized antibodies. U.S. Pat. No. 6,639,055.
9. Chothia, C., Lesk, A. M. 1987. Canonical structures for the hypervariable regions of immunoglobulins. J Mol Biol 196:901-917.
10. D'Argenio, D. Z., Schumitzky, A. 1979. A program package for simulation and parameter estimation in pharmacokinetic systems. Comput Programs Biomed 9:115-134.
11. Eigenbrot, C., Randal, M., Presta, L., Carter, P., Kossiakoff, A. A. 1993. X-ray structures of the antigen-binding domains from three variants of humanized anti-p185HER2 antibody 4D5 and comparison with molecular modeling. J Mol Biol 229:969-995.
12. Eigenbrot, C., et al. 1994. X-Ray structures of fragments from binding and nonbinding versions of a humanized anti-CD18 antibody: structural indications of the key role of VH residues 59 to 65. Proteins 18:49-62.
13. Foote, J., Winter, G. 1992. Antibody framework residues affecting the conformation of the hypervariable loops. J Mol Biol 224:487-499.
14. Gibrat, J. F., Madej, T., Bryant, S. H. 1996. Surprising similarities in structure comparison. Curr Opin Struct Biol 6:377-385.
15. Horton, R. M., Hunt, H. D., Ho, S. N., Pullen, J. K., Pease, L. R. 1989. Engineering hybrid genes without the use of restriction enzymes: gene splicing by overlap extension. Gene 77:61-68.
16. Huang, E. H., Kaufman, H. L. 2002. CEA-based vaccines. Expert Rev Vaccines 1:49-63.
17. Imikare, T., et al. 2004. Generation, immunologic characterization and antitumor effects of human monoclonal antibodies for carcinoembryonic antigen. Int J Cancer 108:564.
18. Johnson, G., Wu, T. T. 2001. Kabat database and its applications: future directions. Nucleic Acid Res 29:205-206.
19. Jones, P. T., Dear, P. H., Foote, J., Neuberger, M. S., Winter, G. 1986. Replacing complementarity-determining regions in a human antibody with those from a mouse. Nature 321:522-525.
20. Laemmli, U. 1970. Cleavage of structural protein during the assembly of the head of bacteriophage T4. Nature 227:680-685.
21. Low, N. M., Holliger, P. H., Winter, G. 1986. Mimicking somatic hypermutation: affinity maturation. J Mol Biol 260:359-368.
22. MacCallum, R. M., Martin, A. C., Thornton, J. M. 1996. Antibody-antigen interactions: contact analysis and binding site topography. J Mol Biol 262:732-745.
23. Marshall, J. 2003. Carcinoembryonic antigen-based vaccines. Semin Oncol 30(3 Suppl 8):30-36
24. Maynard J., Georgiou, G. 2000. Antibody engineering. Annu Rev Biomed Eng 2:339-376.
25. Mendez, M. J., et al. 1997. Functional transplant of megabase human immunoglobulin loci recapitulates human antibody response in mice. Nat Genet. 2:146-156.
26. Morea, V. T. A., Rustici, M., Chothia, C., Lesk, A. M. 1998. Conformations of the third hypervariable region in the VH domain of immunoglobulins. J Mol Biol 275:269-294.
27. Morton, B. A., O'Connor-Tressel, M., Beatty, B. G., Shively, J. E., Beatty, J. D. 1988. Artifactual CEA elevation due to human anti-mouse antibodies. Arch Surg 123:1242-1246.
28. Neumaier, M., et al. 1990. Cloning of the genes for T84.66, an antibody that has a high specificity and affinity for carcinoembryonic antigen, and expression of chimeric human/mouse T84.66 genes in myeloma and Chinese hamster ovary cells. Cancer Res 50:2128-2134.
29. O'Brien, S., Jones, T. 2003. Humanization of monoclonal antibodies by CDR grafting. Methods Mol Biol 207:81-100.
30. O'Connor, S. J., Meng, Y. G., Rezaie, A. R., Presta, L. G. 1998. Humanization of an antibody against human protein C and calcium-dependence involving framework residues. Protein Eng 11:321-328.
31. Padlan, E. A., Abergel, C., Tipper, J. P. 1995. Identification of specificity-determining residues in antibodies. FASEB J 9:133-139.
32. Pedersen, J. T., et al. 1997. Resurfacing of rodent antibodies. U.S. Pat. No. 5,639,641.
33. Schroff, R. W., Foon, K. A., Beatty, S. M., Oldham, R. K., and Morgan, A. C. Jr.

33. Shawler, D. L., Bartholomew, R. M., Smith, L. M., and Dillman, R. O. 1985. Human anti-murine responses in patients receiving monoclonal antibody therapy. Cancer Res 45:879-885.
34. Shawler, D. L., Bartholomew, R. M., Smith, L. M., and Dillman, R. O. 1985. Human immune responses to multiple injections of murine monoclonal immunoglobulins. J Immunol 135:1530-1535.
35. Wagener, C., Clark, B. R., Rickard, K. J., Shively, J. E. 1983. Monoclonal antibodies for carcinoembryonic antigen and related antigens as a model system: determination of affinities and specificities of monoclonal antibodies by using biotin-labeled antibodies and avidin as precipitating agents in a solution phase immunoassay. J Immunol 130: 2302-2307.
36. Winter, G., Griffiths, A. D., Hawkins, R. E., Hoogenboom, H. R. 1994. Making antibodies by phage display technology. Annu Rev Immunol 12:433-455.
37. Wong, J. Y. C., et al. 1995. Initial experience evaluating $^{90}$yttrium-radiolabeled anti-carcinoembryonic antigen chimeric T84.66 in a phase I radioimmunotherapy trial. Cancer Res 55(23 Suppl): 5929s-5934s.
38. Wong, J. Y. C., et al. 1997. Clinical evaluation of indium-111-labeled chimeric anti-CEA monoclonal antibody. J Nucl Med 38:1951-1959.
39. Wong, J. Y. C., et al. 1999. Initial clinical experience evaluating yttrium-90-chimeric T84.66 anticarcinoembryonic antigen antibody and autologous hematopoietic stem cell in patients with carcinoembryonic antigen-producing metastatic breast cancer. Clin Cancer Res 5(10 Suppl): 3224s-3231s.
40. Wu, T. T., Kabat, E. A. 1970. An analysis of the sequences of the variable regions of Bence Jones proteins and myeloma light chains and their implications for antibody complementarity. J Exp Med 132:211-250.
41. Wu, A. M., et al. 1996. Tumor localization of anti-CEA single-chain Fvs: improved targeting by noncovalent dimers. Immunotechnology 2:221-236.
42. Xiang, J., Sha, Y., Jia, Z., Prasad, L., Delbaere, L. T. 1995. Framework residues 71 and 93 of the chimeric B72.3 antibody are major determinants of the conformation of heavy-chain hypervariable loops. J Mol Biol 253:385-390.
43. Yazaki, P. J., et al. 2001. Mammalian expression and hollow fiber bioreactor production of recombinant anti-CEA diabody and minibody for clinical applications. J Immunol Methods 253:195-208.
44. Young, H. Y., Hefta, L. J., Yazaki, P. J., Wu, A. M., Shively, J. E. 1998. Expression, purification, and characterization of a two domain carcinoembryonic antigen minigene (N-A3) in *Pichia pastoris*. The essential role of the N-domain. Anticancer Res 18:3192-3202.

What is claimed is:

1. A method of treating a subject having a tumor expressing CEA, comprising administering to said subject a humanized antibody comprising:
   a) a variable light chain of a humanized antibody 4D5 version 8, wherein the L4, L24-L34, L50-L56, L66-L69, and L89-L97 residues of said humanized antibody 4D5 version 8 variable light chain (residues 4, 24-34, 50-56, 66-69, and 89-97, respectively of SEQ ID NO:6) have been replaced with a corresponding set of residues from the murine T84.66 monoclonal antibody variable light chain (residues 4, 24-38, 54-60, 70-73, and 93-101, respectively, or SEQ ID NO:4); and
   b) a variable heavy chain of a humanized antibody 4D5 version 8, wherein the H30-H35, H50-H58, and H93-H102 residues of said humanized antibody 4D5 version 8 variable heavy chain (residues 30-35, 50-58, and 93-102, respectively of SEQ ID NO:7) have been replaced with a corresponding set of residues from the murine T84.66 monoclonal antibody variable heavy chain (residues 30-35, 50-59, and 97-110, respectively, of SEQ ID NO:5); wherein said humanized antibody recognizes the same epitope as the murine monoclonal antibody T84.66.

2. The method of claim 1, wherein said humanized antibody comprises:
   a) a light chain variable region comprising the amino acid sequence of SEQ ID NO: 1; and
   b) a heavy chain variable region comprising the amino acid sequence of SEQ ID NO: 2.

3. The method of claim 1, wherein said humanized antibody comprises:
   a) a light chain variable region comprising the amino acid sequence of SEQ ID NO: 1; and
   b) a heavy chain variable region comprising the amino acid sequence of SEQ ID NO: 3.

4. The method of claim 1, wherein said humanized antibody further comprises a conjugate.

5. The method of claim 4, wherein said conjugate is selected from the group consisting of a toxin, a chemotherapeutic agent, a radiolabel, and a cytokine.

6. The method of claim 1, wherein binding of said humanized antibody to the surface of said tumor stimulates an immune response against said tumor.

7. A method of inhibiting the growth of a tumor expressing CEA, comprising administering a humanized antibody comprising:
   a) a variable light chain of a humanized antibody 4D5 version 8, wherein the L4, L24-L34, L50-L56, L66-L69, and L89-L97 residues of said humanized antibody 4D5 version 8 variable light chain (residues 4, 24-34, 50-56, 66-69, and 89-97, respectively of SEQ ID NO:6) have been replaced with a corresponding set of residues from the murine T84.66 monoclonal antibody variable light chain (residues 4, 24-38, 54-60, 70-73, and 93-101, respectively, or SEQ ID NO:4); and
   b) a variable heavy chain of a humanized antibody 4D5 version 8, wherein the H30-H35, H50-H58, and H93-H102 residues of said humanized antibody 4D5 version 8 variable heavy chain (residues 30-35, 50-58, and 93-102, respectively of SEQ ID NO:7) have been replaced with a corresponding set of residues from the murine T84.66 monoclonal antibody variable heavy chain (residues 30-35, 50-59, and 97-110, respectively, or SEQ ID NO:5); humanized antibody recognizes the same epitope as the murine monoclonal antibody T84.66.

8. The method of claim 7, wherein said humanized antibody comprises:
   a) a light chain variable region comprising the amino acid sequence of SEQ ID NO: 1; and
   b) a heavy chain variable region comprising the amino acid sequence of SEQ ID NO: 2.

9. The method of claim 7, wherein said humanized antibody comprises:
   a) a light chain variable region comprising the amino acid sequence of SEQ ID NO: 1; and
   b) a heavy chain variable region comprising the amino acid sequence of SEQ ID NO: 3,
   c) a light chain constant region comprising elements of one or more human immunoglobulin light chain constant regions; and
   d) a heavy chain constant region comprising elements of one or more human immunoglobulin heavy chain constant regions.

* * * * *